(12) United States Patent
Weber et al.

(10) Patent No.: US 12,318,625 B2
(45) Date of Patent: Jun. 3, 2025

(54) LIGHT APPLICATOR

(71) Applicant: Richard Wolf GmbH, Knittlingen (DE)

(72) Inventors: Bernd Claus Weber, Karlsruhe (DE); Manfred Wirth, Dresden (DE)

(73) Assignee: RICHARD WOLF GMBH, Knittlingen (DE)

( * ) Notice: Subject to any disclaimer, the term of this patent is extended or adjusted under 35 U.S.C. 154(b) by 554 days.

(21) Appl. No.: 17/634,650

(22) PCT Filed: Aug. 13, 2020

(86) PCT No.: PCT/DE2020/200069
§ 371 (c)(1),
(2) Date: Feb. 11, 2022

(87) PCT Pub. No.: WO2021/027998
PCT Pub. Date: Feb. 18, 2021

(65) Prior Publication Data
US 2022/0355126 A1 Nov. 10, 2022

(30) Foreign Application Priority Data

Aug. 14, 2019 (DE) ...................... 10 2019 212 199.3

(51) Int. Cl.
*A61N 5/06* (2006.01)
*A61B 1/00* (2006.01)
*A61B 18/00* (2006.01)

(52) U.S. Cl.
CPC .......... *A61N 5/0601* (2013.01); *A61N 5/062* (2013.01); *A61B 1/00114* (2013.01);
(Continued)

(58) Field of Classification Search
CPC ................. A61N 5/0601; A61N 5/062; A61N 2005/0651; A61B 1/00114; A61B 2018/00095; A61B 2018/00101
See application file for complete search history.

(56) References Cited

U.S. PATENT DOCUMENTS 5,817,015 A * 10/1998 Adair ................. A61B 1/00174
600/182
5,976,075 A * 11/1999 Beane .................. A61B 5/6864
600/106
(Continued)

FOREIGN PATENT DOCUMENTS

CN 105072969 A 11/2015
DE 102018202243 A1 8/2019
(Continued)

*Primary Examiner* — Catherine M Voorhees
(74) *Attorney, Agent, or Firm* — McGlew and Tuttle, P.C.

(57) ABSTRACT

A light applicator (5) for examining and/or treating an organic body includes a minimal-invasive, rigid, semi-flexible or flexible insertion section (11) which extends along a longitudinal direction (L) and at its distal end includes an LED (19). The light applicator (5) includes a first electrical lead (61a) for the supply of electricity to the LED (19). The lead extends in the insertion section (11) in the longitudinal direction (L) and there has a cross-sectional area of at least 70% of the cross-sectional area of the light applicator (5). The light applicator (5) in the insertion section (11) is thermally insulated in the radial direction in a manner such that the radial thermal insulation reduces proximally.

31 Claims, 28 Drawing Sheets

(52) U.S. Cl.
CPC ............... *A61B 2018/00095* (2013.01); *A61B 2018/00101* (2013.01); *A61N 2005/0651* (2013.01)

(56) References Cited

U.S. PATENT DOCUMENTS

| | | | |
|---|---|---|---|
| 2011/0092772 A1* | 4/2011 | Weber ................... | A61B 1/128 600/178 |
| 2014/0188035 A1 | 7/2014 | Ehrenreich et al. | |
| 2016/0000309 A1* | 1/2016 | Weber ................... | A61B 1/12 600/179 |
| 2016/0074095 A1* | 3/2016 | Strobl ................. | A61B 18/1445 606/51 |
| 2016/0151639 A1 | 6/2016 | Scharf et al. | |
| 2016/0213945 A1 | 7/2016 | Burwell et al. | |
| 2020/0138271 A1* | 5/2020 | Toth .................... | A61B 1/0676 |
| 2020/0178784 A1* | 6/2020 | Hoyle ................... | A61B 1/055 |
| 2021/0386443 A1* | 12/2021 | Heimberger ........... | A61B 1/018 |

FOREIGN PATENT DOCUMENTS

| | | | |
|---|---|---|---|
| EP | 2449994 A1 | 5/2012 | |
| EP | 3210521 A1 | 8/2017 | |

\* cited by examiner

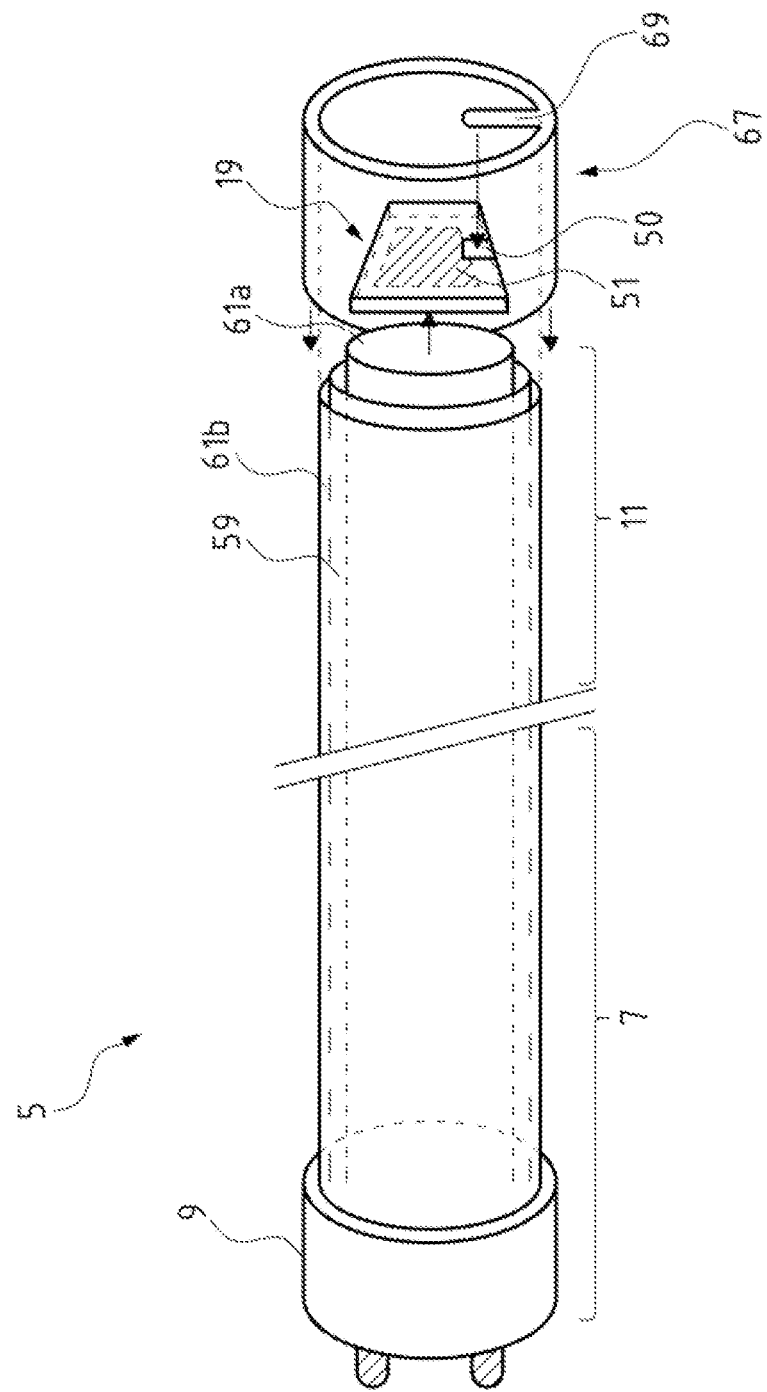

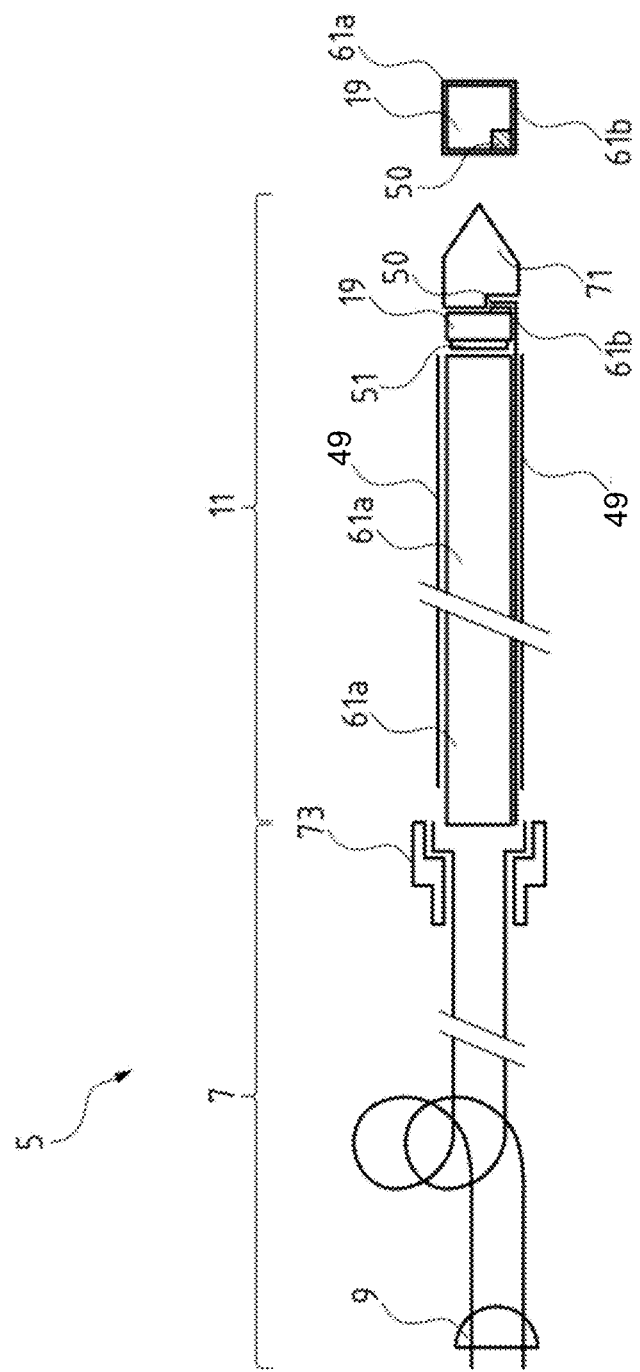

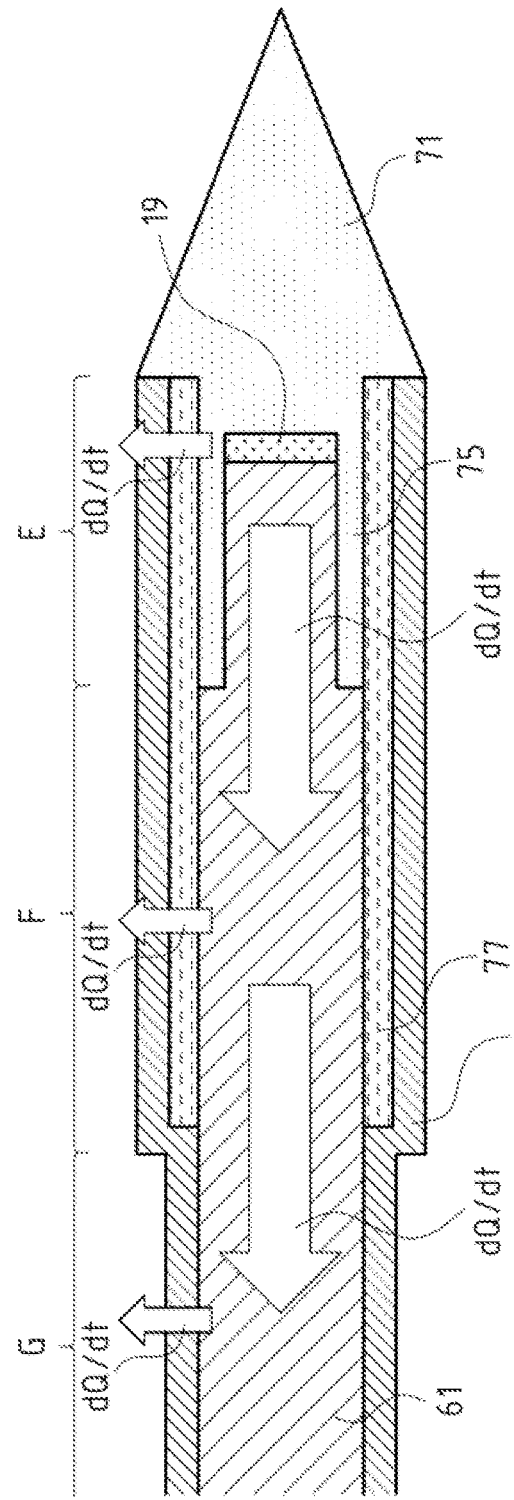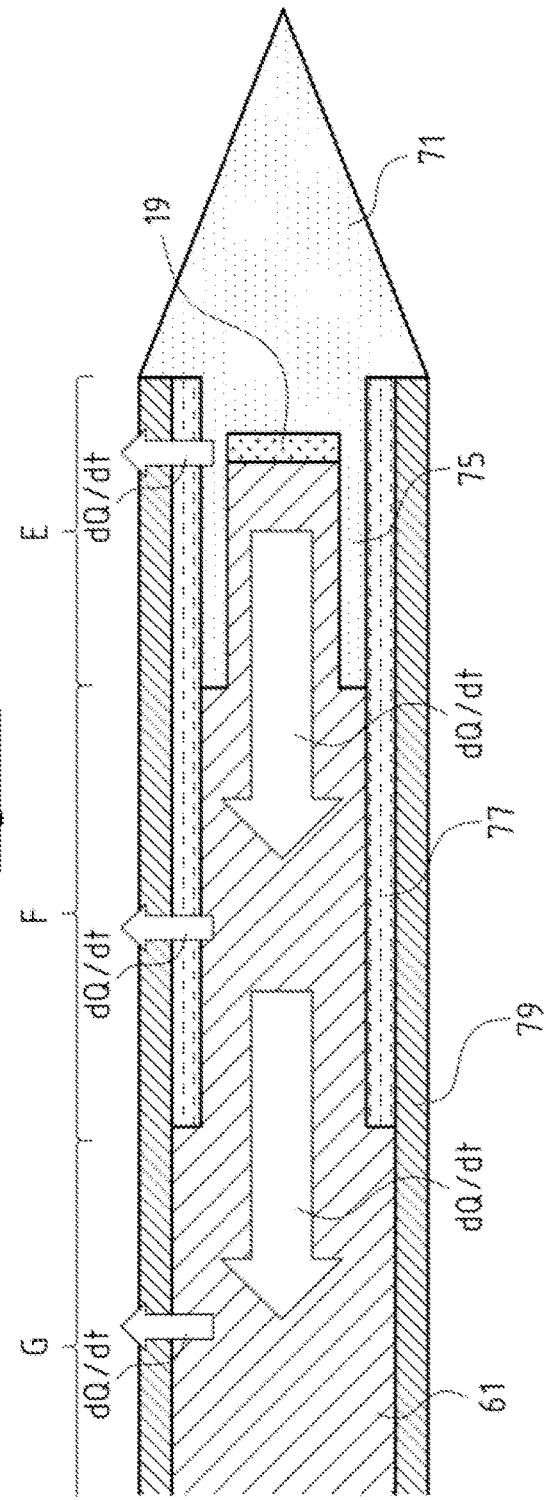

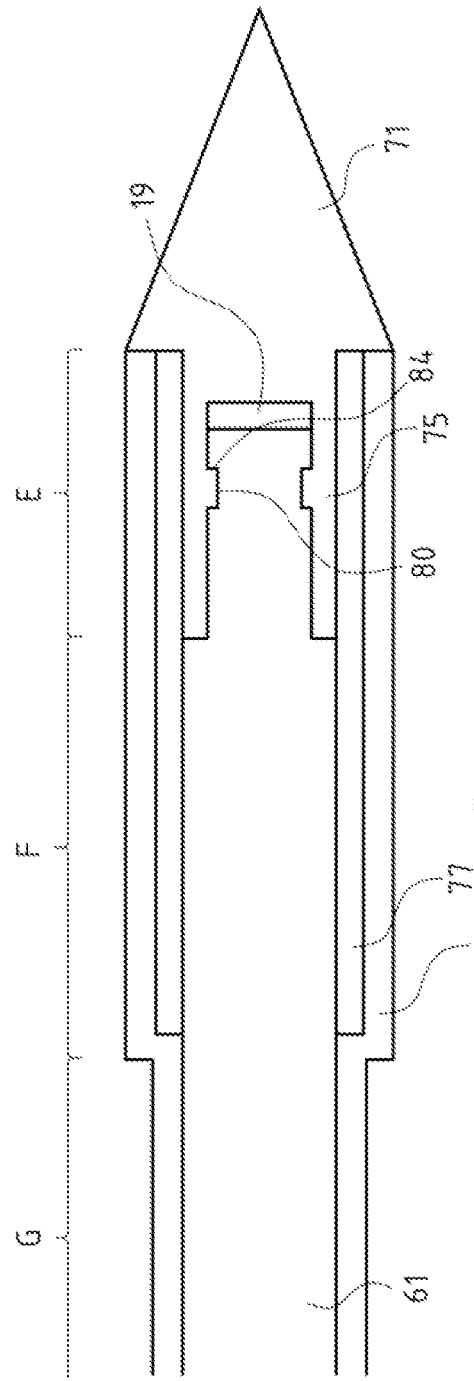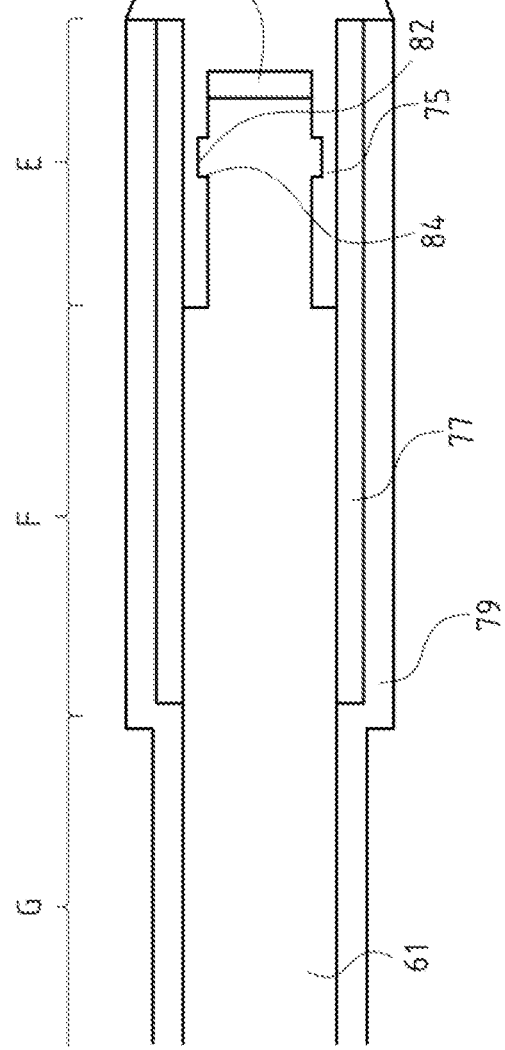

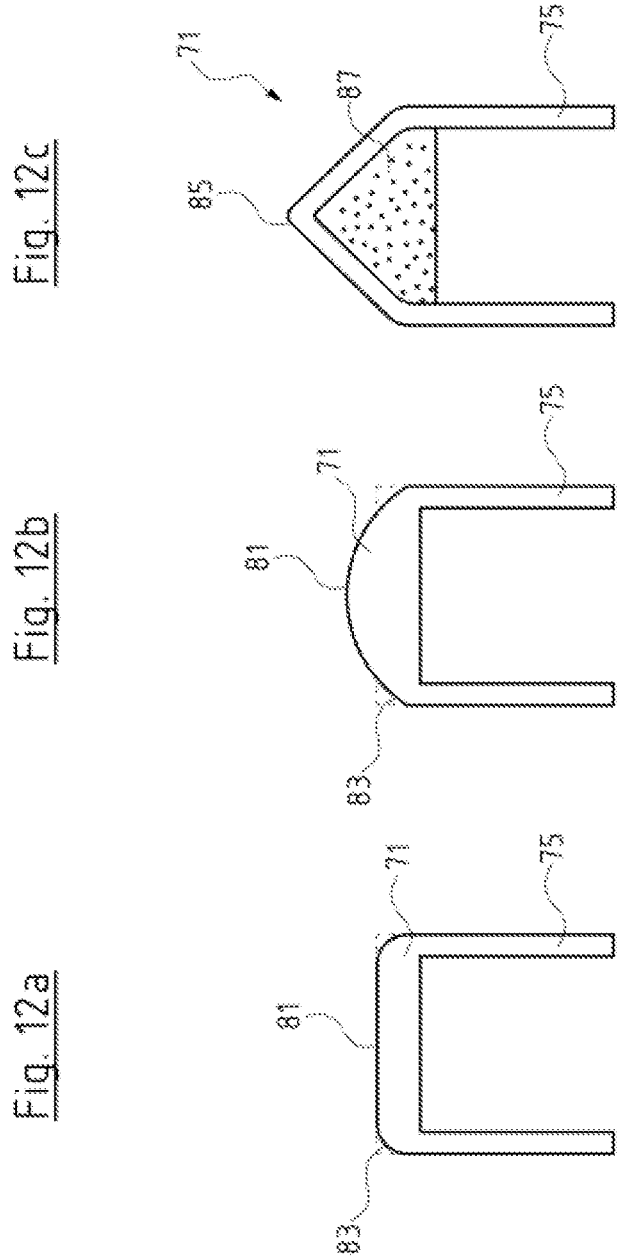

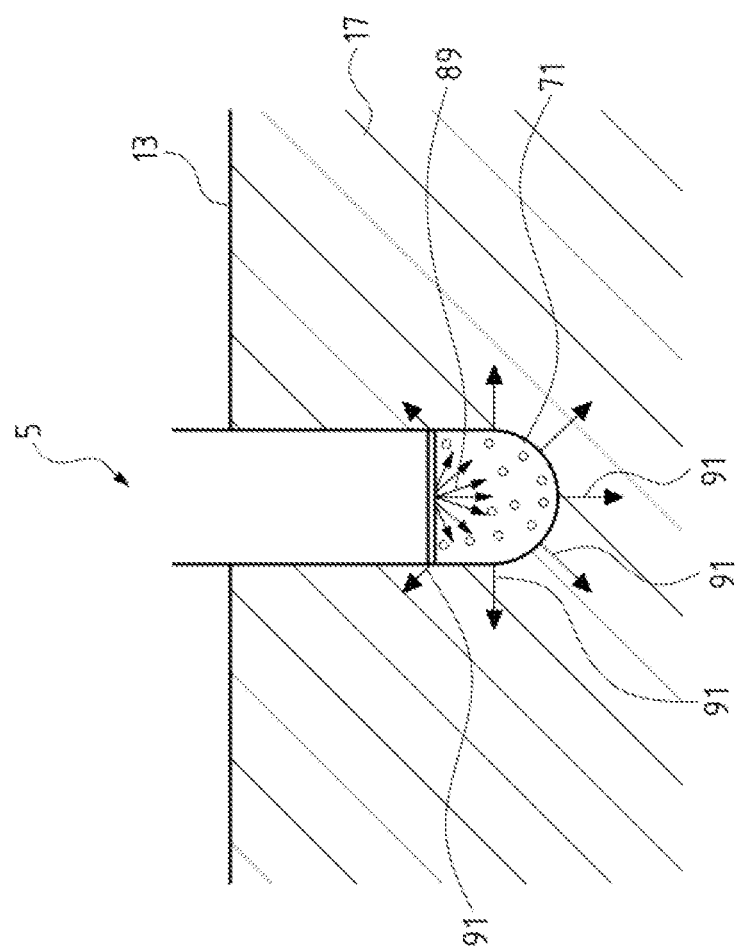

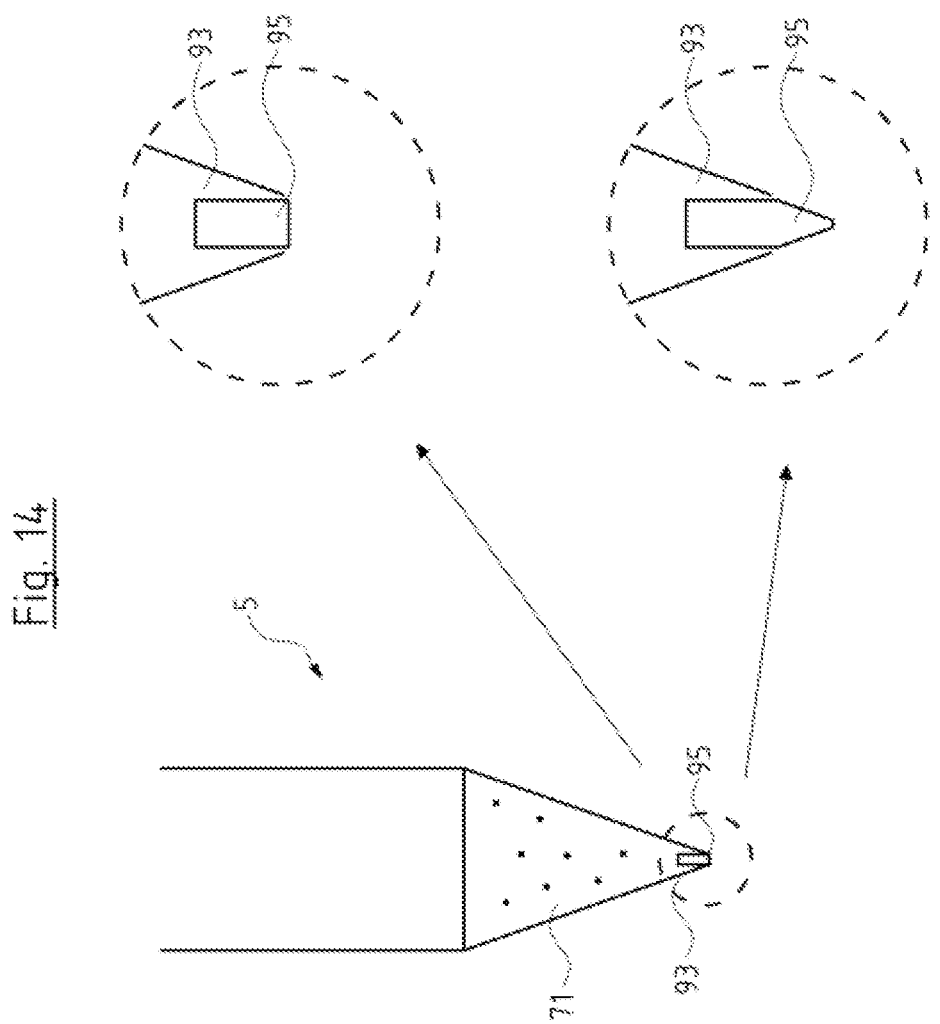

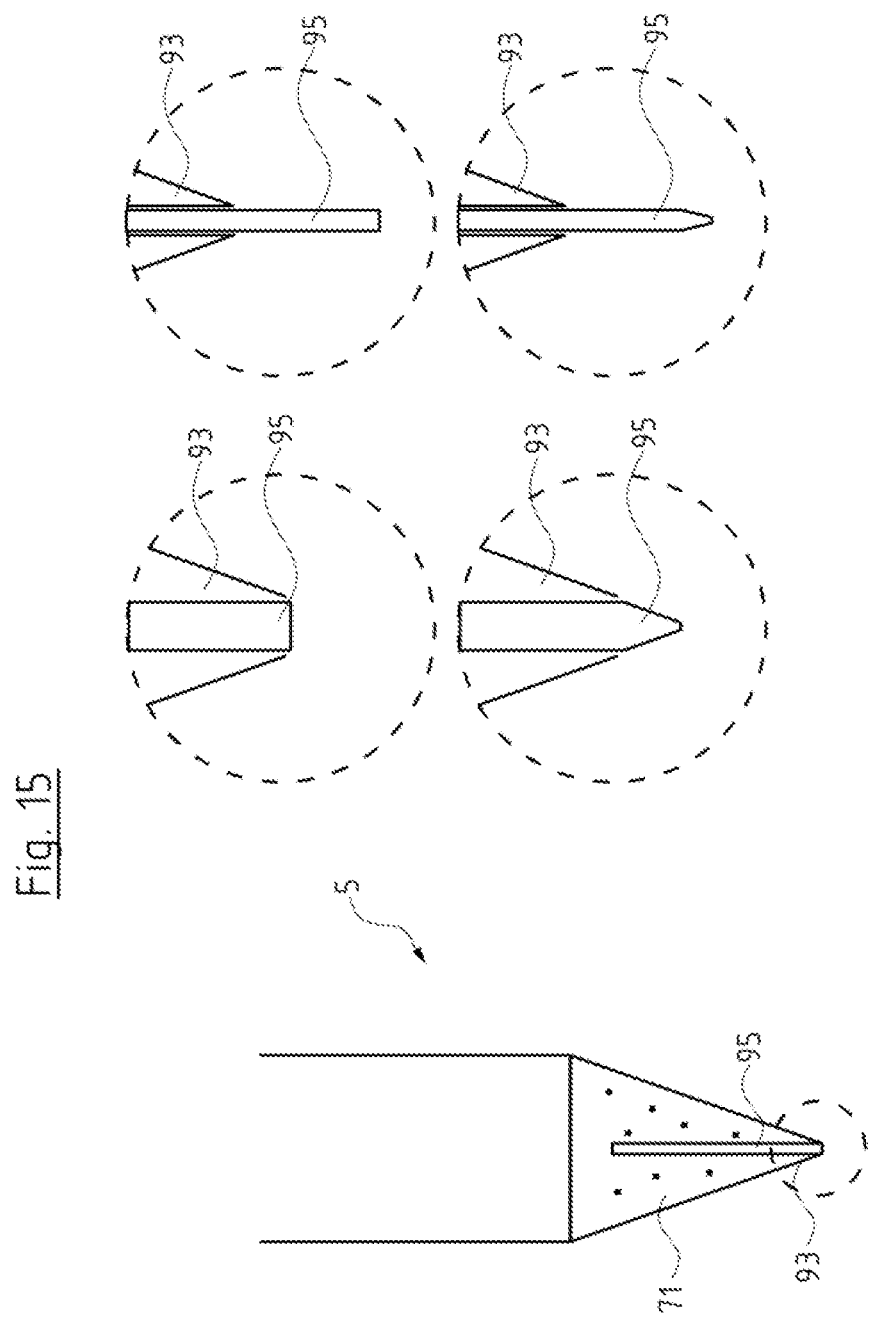

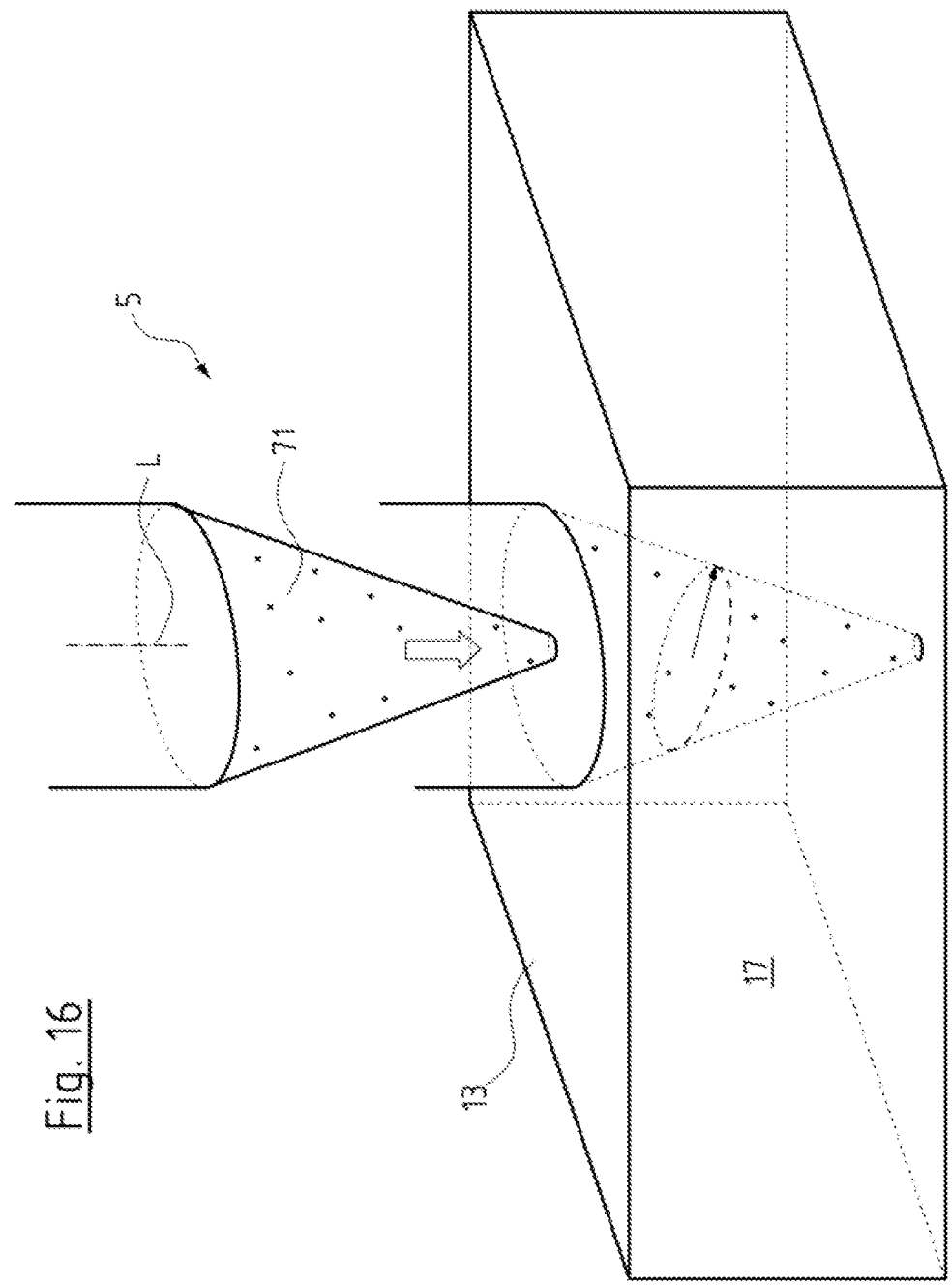

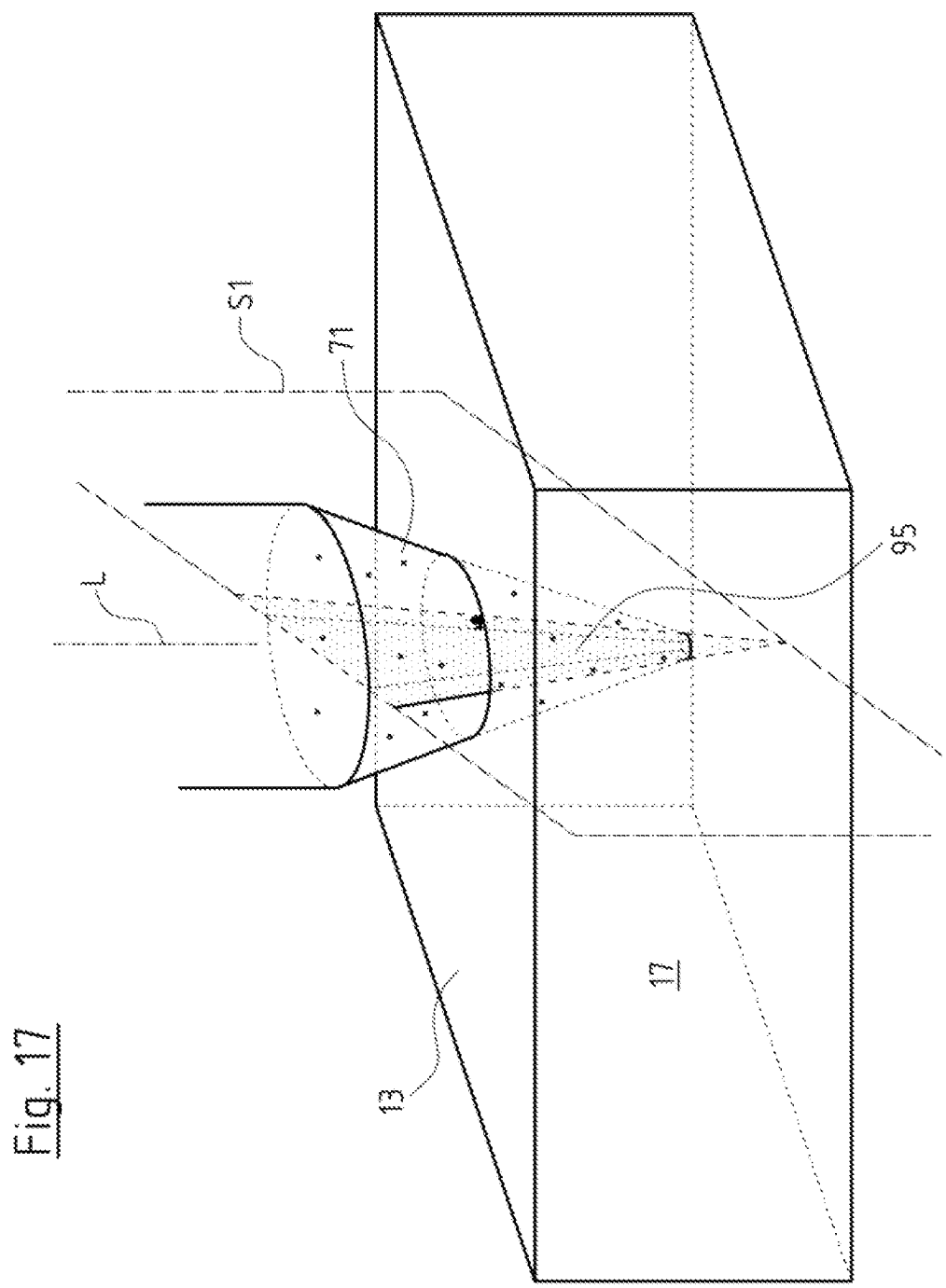

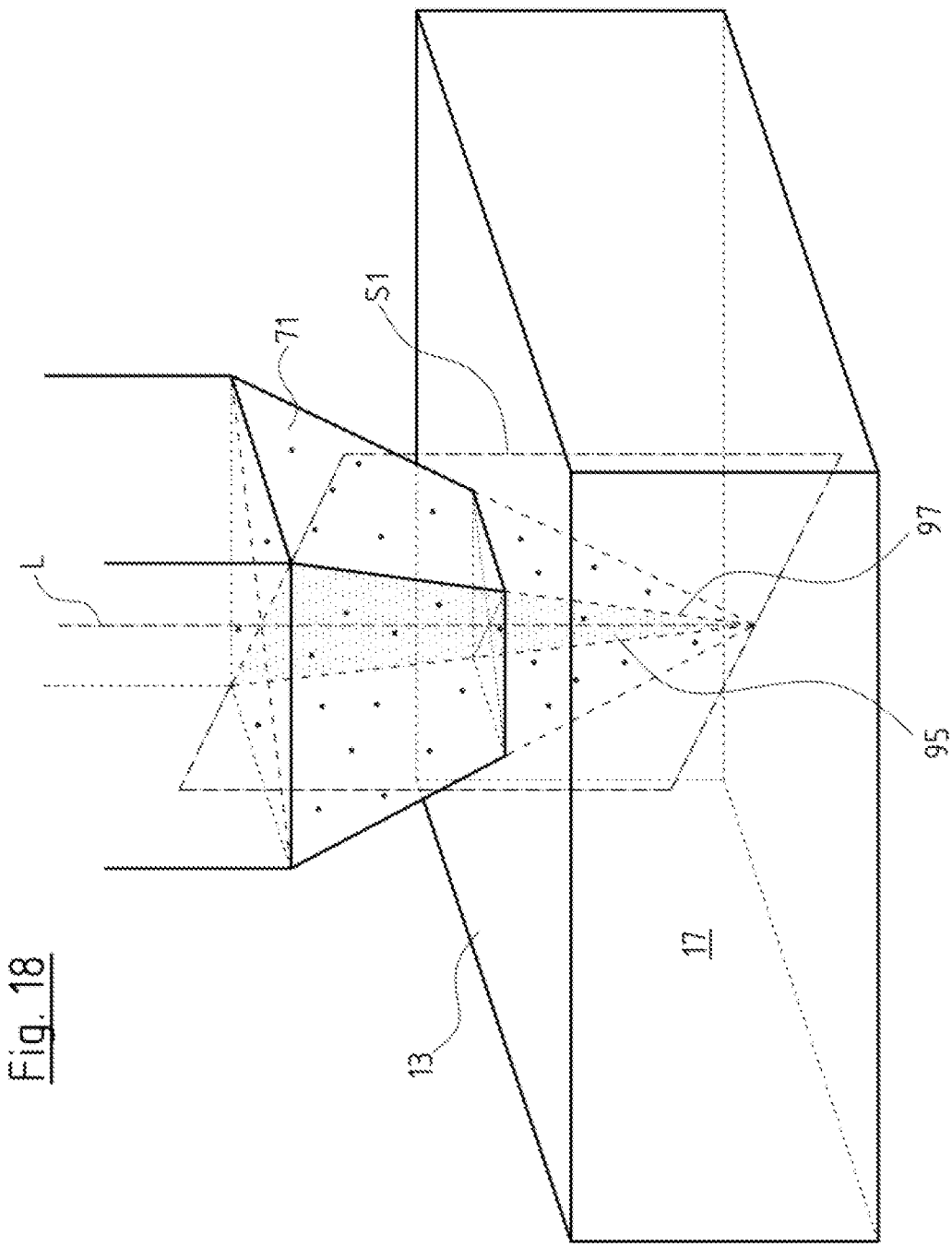

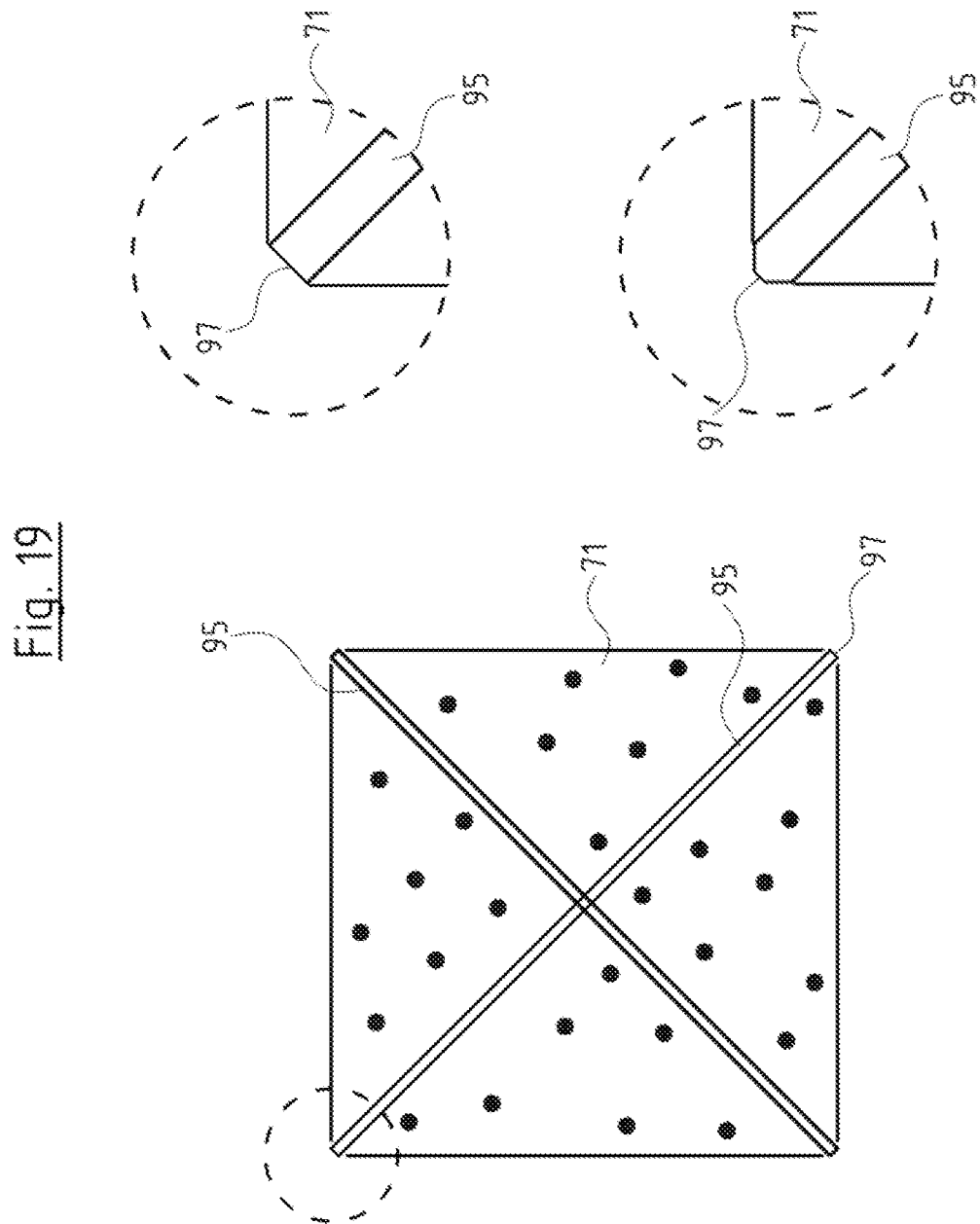

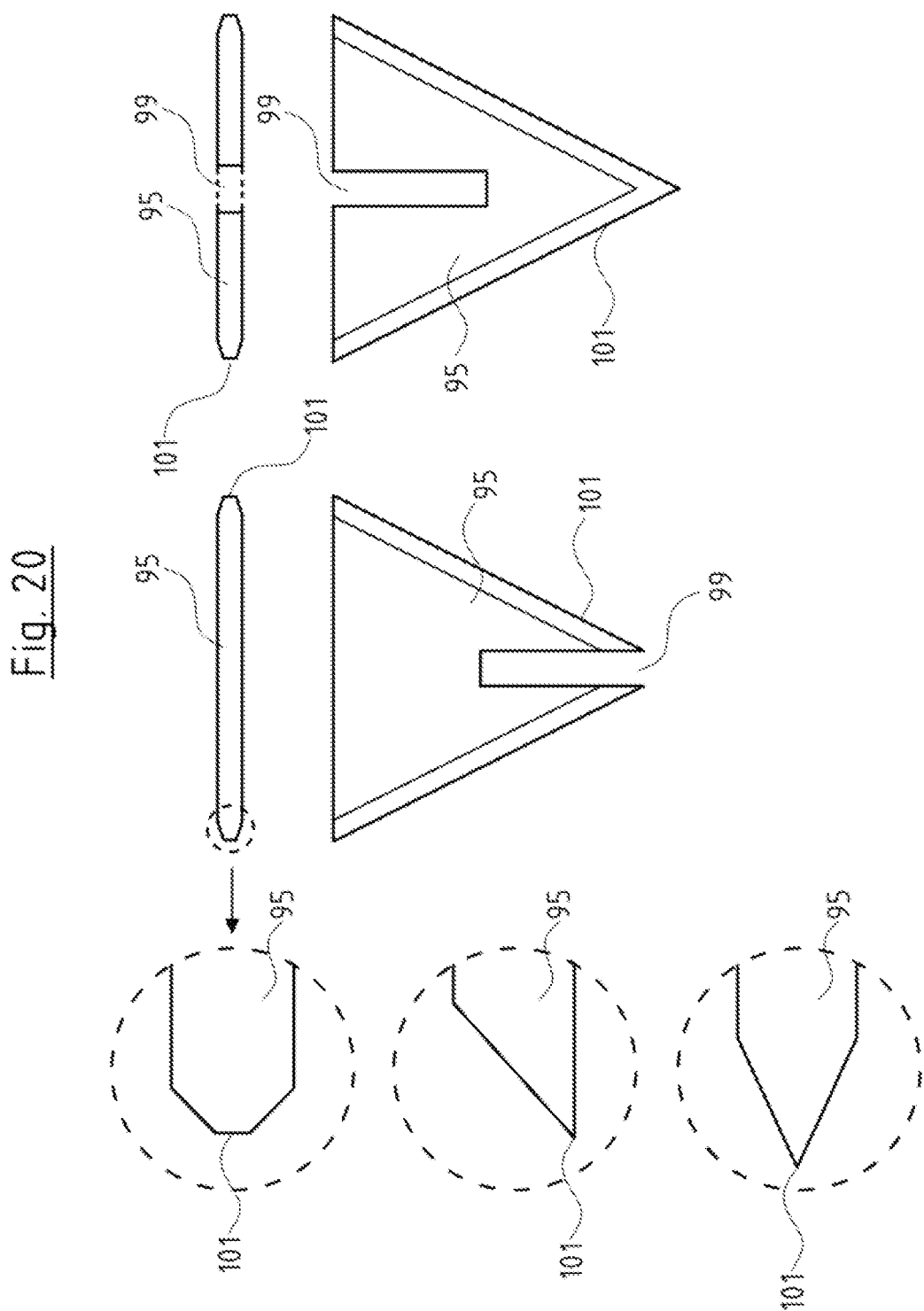

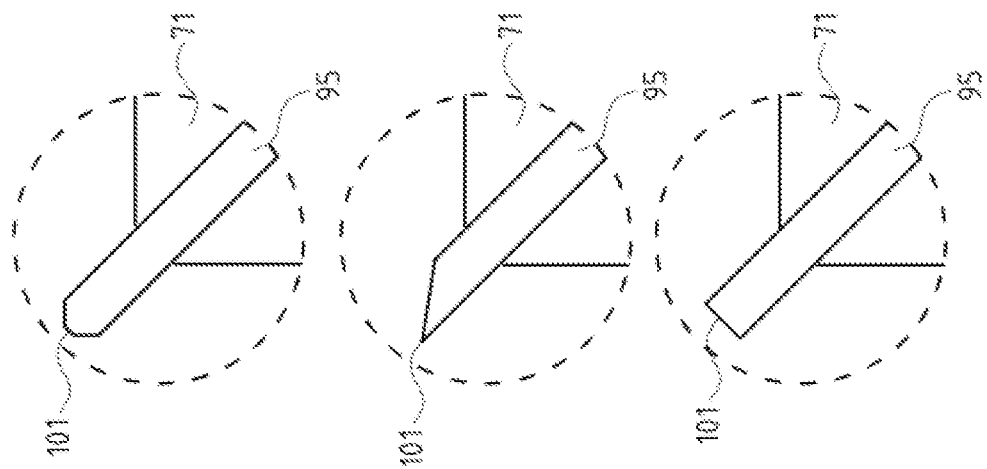
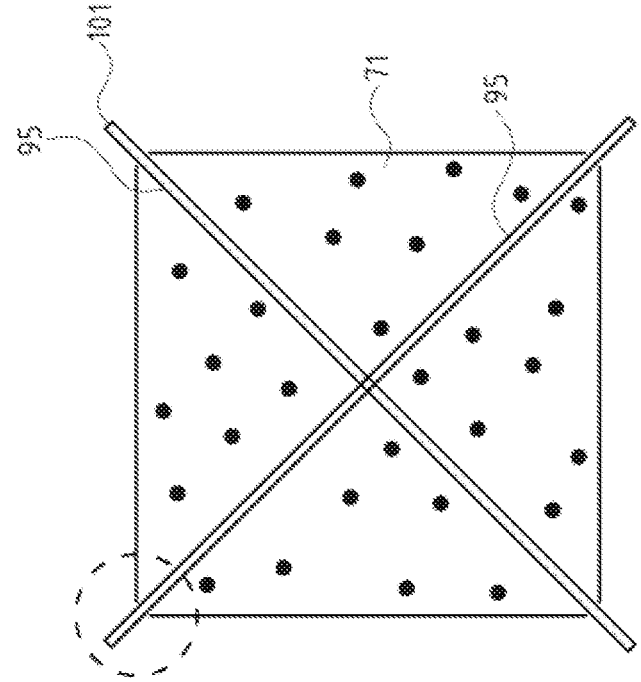
Fig. 22

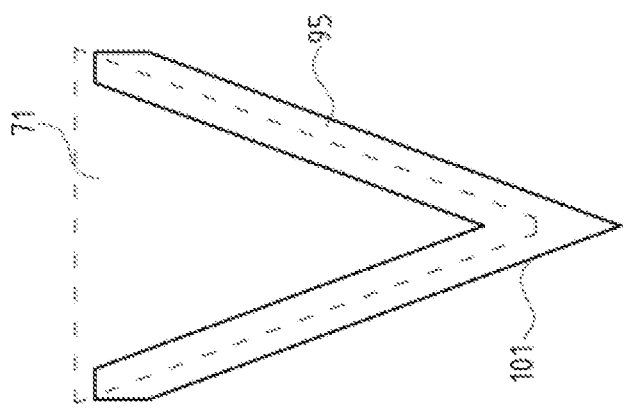

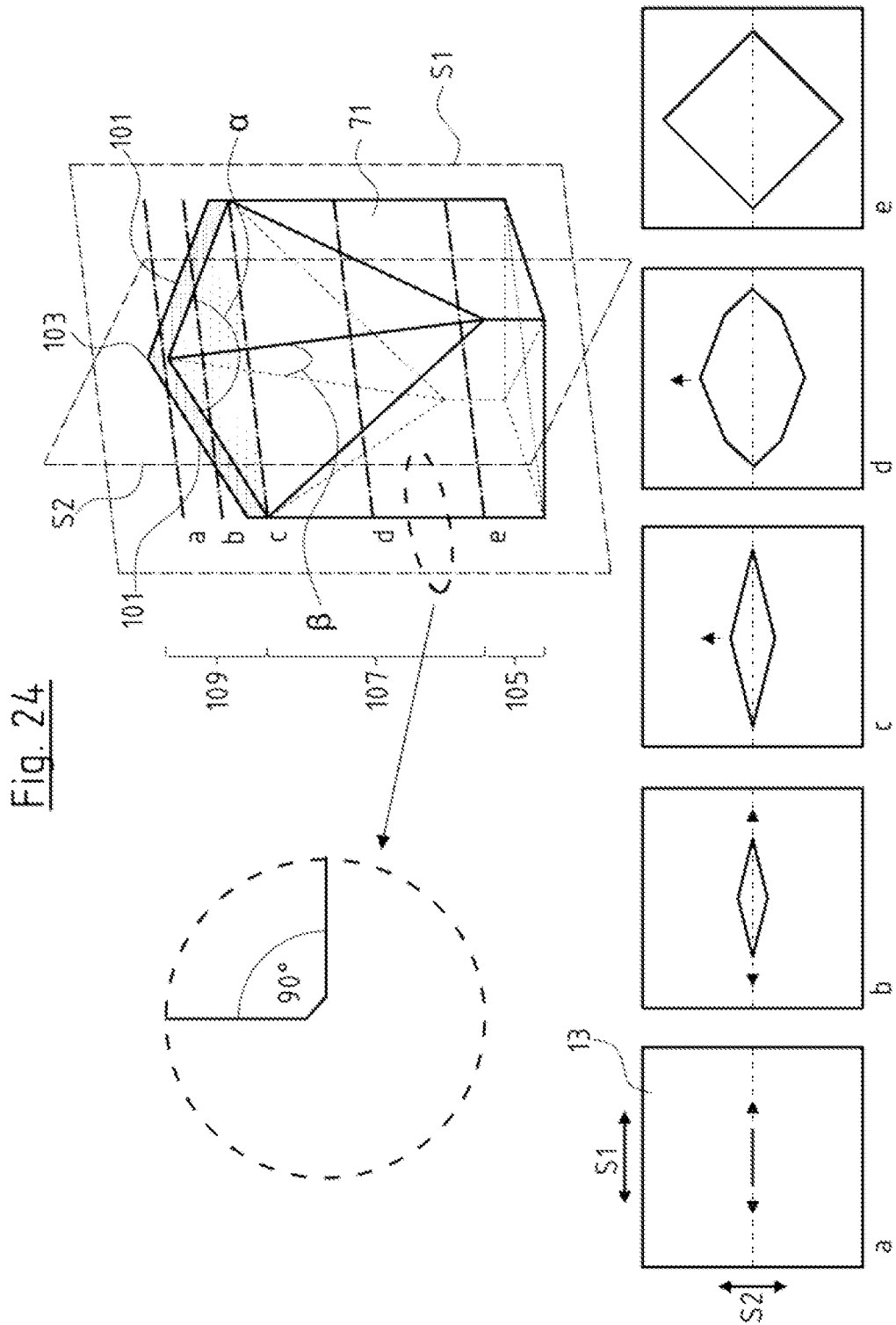

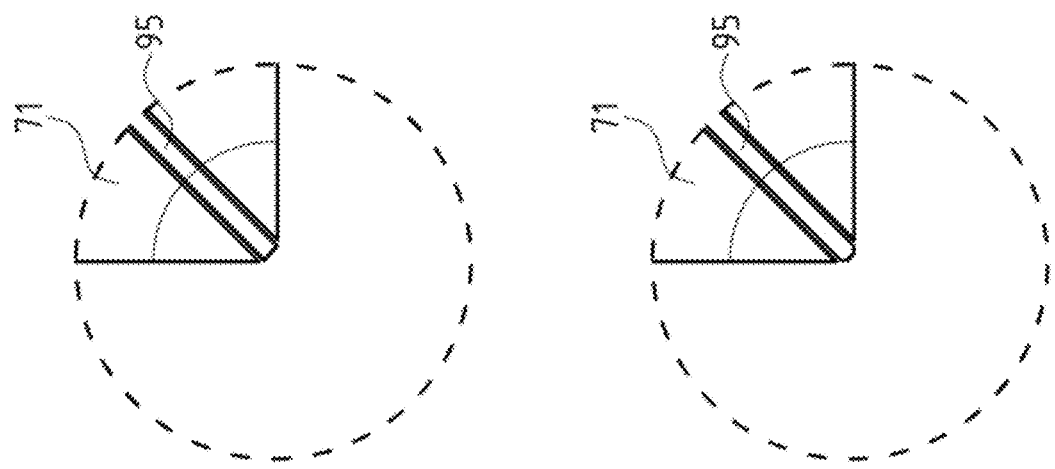
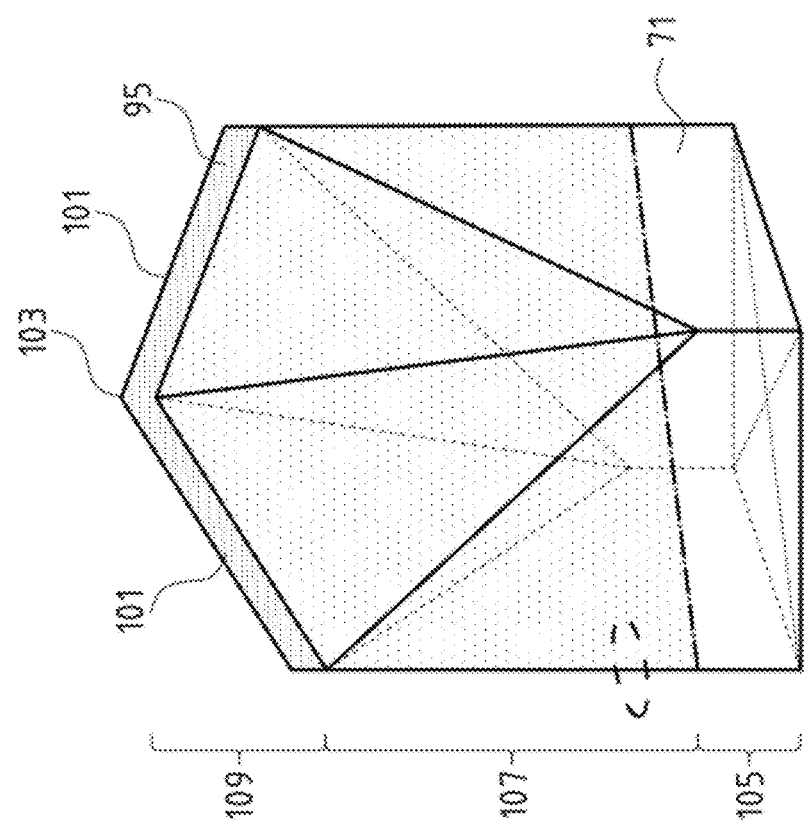

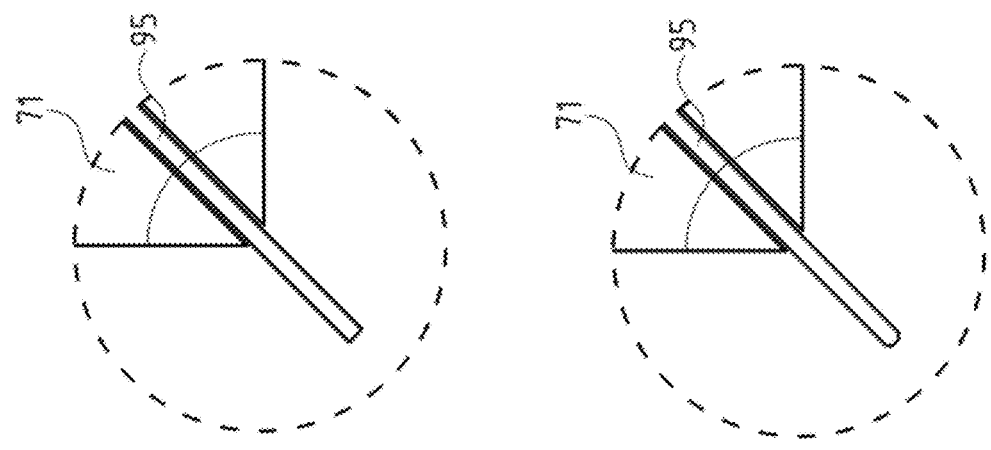
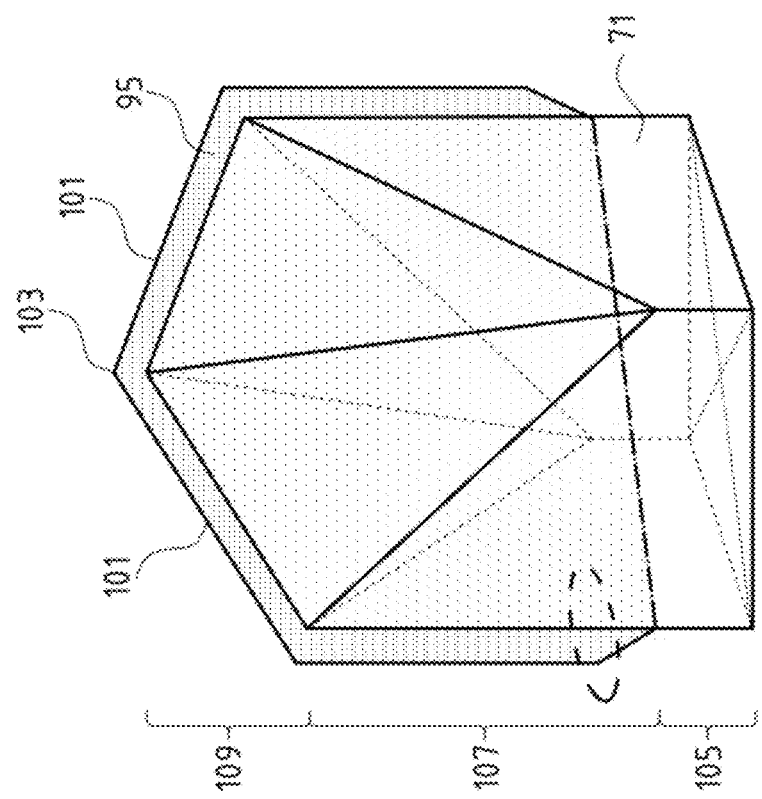
Fig. 26

LIGHT APPLICATOR

CROSS REFERENCE TO RELATED APPLICATIONS

This application is a United States National Phase Application of International Application PCT/DE2020/200069, filed Aug. 13, 2020, and claims the benefit of priority under 35 U.S.C. § 119 of German Application 10 2019 212 199.3, filed Aug. 14, 2019, the entire contents of which are incorporated herein by reference.

TECHNICAL FIELD

The present disclosure relates to a light applicator for examining and/or treating an organic body, in particular for the photodynamic therapy (PPT) of pathological tissue.

TECHNICAL BACKGROUND

It is known to use endoscopes in order to make video recordings of the inside of a human or animal body for the purposes of medical diagnosis and/or therapy. Herein, one constantly strives to design the insertion section of the endoscopes as thinly a possible, so that one can inspect as small as possible cavities and that the tissue suffers as little as possible injury.

However, endoscopes are not only used in order to make picture and video recordings, but also as diagnosis means or therapy means itself. For example, fluorescence endoscopy can be used for the detection and localisation of premalignant and early malignant tissue, concerning which is not a question of natural real-colour representation of the tissue, but merely a fluorescence excitation with which pathological tissue can be differentiated from healthy tissue. Herein, the pathological tissue which is excited by way of light radiation or a bacterial accumulation which points to pathological tissue can fluoresce in a specific manner and thus be recognisably localised with respect to the surrounding healthy tissue. Fluorescence endoscopy can be carried out for example in the course of a photodynamic diagnosis (PDD) and/or photodynamic therapy (PDT) by way of a photo-sensibiliser or marker substance (e.g. Chlorin e6) which selectively enriches on pathological tissue.

With regard to photodynamic therapy (PDT), light is applied directly onto or even into pathological tissue by way of a light applicator, in order in a light-induced manner to encourage the formation of oxygen radicals by way of the photo-sensibiliser or marker substance which is enriched in a locally limited manner and by way of this to destroy the pathological tissue, such as a tumour. For this, typically laser light is coupled into a fibre optic and is led to the tissue. If the pathological tissue is arranged in an extensive manner on an outer surface, e.g. the skin or an inner surface, e.g. oesophagus inner surface or gut wall, then the therapy light can be coupled out in a relatively simple manner and be beamed onto the pathological tissue surface. However, if the pathological tissue extends over a volume, then on account of the limited penetration depth of the light into the tissue, a tumour cannot always be effectively irradiated from the "outside". In this case, PDT is particularly effective if the light is irradiated from the inside of the pathological tissue volume as isotropically as possible. For this, the light applicator must be pierced into the pathological tissue. This is also denoted as interstitial (through inner surfaces) and/or percutaneous (through the skin) PDT.

In EP 2 449 994 A1 it is described for example how a light applicator in the form of a laser fibre optic is inserted into pathological tissue, after the path for the fibre optic has be pre-pierced through the tissue with a needle.

The disadvantage with this known solution on the one hand is the fact that the coupling of the light out of a thin distal fibre optic end is not bundled in an isotropic manner, but in a highly distal manner. On the other hand, the thin laser fibre optic is itself very pliable, by which means it must be led as far as possible up to the pathological tissue by way of a rigid channel guide and cannot be pushed far out of the channel guide without it bending. On piercing, depending on the penetration depth, possibly high resistances of the healthy tissue and pathological tissue, through which one penetrate, must be overcome, so that the possible penetration depth with the known solution is very limited. Furthermore, the known solution is relatively complex and expensive, so that it cannot be realised as a disposable article for single use.

From this results the object of providing a more economical light applicator which permits a more effective spatial illumination for interstitial and/or percutaneous PDT.

SUMMARY

According a first aspect of the present disclosure, for solving this problem, a light applicator for examining and/or treating an organic body is provided, wherein the light applicator comprises a minimal-invasive rigid, semi-flexible or flexible insertion section which extends along a longitudinal direction and at its distal end comprises an LED, wherein the light applicator comprises a first electrical lead for the electricity supply of the LED, said lead extending in the insertion section in the longitudinal direction and therefore having a cross-sectional area of at least 70% of the cross-sectional area of the light applicator, wherein the light applicator in the insertion section is thermally insulated in the radial direction in a manner such that the radial thermal insulation decreases proximally.

Concerning the light applicator which is disclosed here, no laser fibre optics are applied, but the therapy light is generated in situ at the distal end of the light applicator by way of a miniaturised LED, e.g. with a lateral width of less than 1 mm. An expensive laser is not therefore necessary. The common irradiation characteristics of an LED according to the Lambert beamer even without the aid of an optical component cover a much greater spatial angle than a laser light coupling-out of a laser fibre optic. If the LED is supplemented at the distal side with an optical component in the form of a scatter body, then a very large spatial angle with a relatively homogenously distributed power can be irradiated, in order to come as close as possible the ideal of an isotropic spatial illumination.

The light applicator which is disclosed herein utilises the electrical lead which is necessary for the electricity supply of the LED, to use the distal end section of the light applicator as a proximalward heat dissipator by way of it being configured so thickly that it takes up a large part of the cross-sectional area of the light applicator. Basically, the in-situ generation of light with an LED entails the disadvantage that the LED generates heat which where possible should not heat the tissue in a harmful manner. The relatively thick electrical lead here functions as a very good thermal conductor in the proximal direction for solving this problem. Due to the proximally reducing radial thermal insulation, the heat is dissipated proximally via the electrical lead in an efficient manner, before the tissue is heated in a harmful manner. For this, the electrical lead can optionally be cooled at the proximal side and/or thermally coupled to a heat sink.

A particularly efficient thermal management is therefore achieved with the proximally reducing radial thermal insulation, which given a low as possible material expense permits a proximalward transport of heat, without herein heating the adjacent tissue in a harmful manner. Technically, there indeed exists the challenge of the LED bringing in a relatively high thermal power and the LED without a sufficient thermal dissipation very quickly assuming damage or at least the optical power which is to be introduced by it reducing with increasing switch-on duration. If for the protection of the surrounding tissue on the one hand one were to simply provide a very high radial thermal insulation over the entire length of the introduction section, the LED would overheat and assume damage, or at least the optical power which is to be mustered by it would reduce. If on the other hand for the protection of the LED one were to simply provide a very weak radial thermal insulation over the entire length of the insertion section, then the surrounding tissue in the region of the LED or in the region of the distal end of the insertion section would heat up too greatly and would assume thermally caused damage. This would also affect healthy tissue if this is located sufficiently close to the LED or the distal end of the insertion section, i.e. the selectivity which characterises the PDT in an advantageous manner given the destruction of tissue, according to which only pathological tissue is destroyed, would be lost in the case of such an applicator. Furthermore, high temperatures at the tissue can cause corresponding high pain, which as the case may be must be combatted by an anesthetising of the patient, which entails an additional effort of the user and an additional burden to the patient. As a solution to this problem, a proximal flow of heat is achieved by way of the proximally reducing radial thermal insulation, and this on the one hand protects the LED from overheating and distributes the lateral dissipation of heat to the surrounding tissue proximally over the insertion section to the extent that the surrounding tissue only heats up to an acceptable extent.

The light applicator which is disclosed here can be manufactured in a very economical manner and thus be realised as a sterile disposable article for single use, which renders expensive cleaning and sterilisation by the user obsolete. Given larger tumours or whole pathological organs or regions or organs, a plurality of light applicators which are disclosed herein can be simultaneously used for PDT by way of them being pierced in a manner distributed over the complete organ, in order to homogenously illuminate the whole organ. Since the photo-sensibiliser or marker substance (e.g. Chlorin e6) selectively enriches only in pathological tissue and reacts there under the influence of light, healthy tissue is not damaged by the light. On the one hand the pathological tissue does not then need to be located beforehand in a very precise manner and on the other hand the risk of the pathological tissue remaining unnoticed and thus not treated is reduced. For percutaneous PDT with several light applicators, it can make sense to provide a possibly organ-specific jig or template which can be placed and/or bonded in front of or onto the skin is a surfaced manner, with organ-specific markings and/or openings, in order to indicate piercing locations, piercing angles and/or piercing depths for the light applicator to the user and to achieve a complete as possible illumination of an organ.

However, not only can the light applicator be used for treating, thus therapy, but also for examining, thus for the diagnosis. It is particularly given an interaction with an endoscope that the fluorescence of a photosensibiliser or marker substance (e.g. Chlorin e6) which is enriched on pathological tissue, said fluorescence being generated by the light applicator, can be observed.

The light applicator can be pushed through a working channel of an endoscopic instrument and be pierced into the tissue with its distal insertion section at the distal end, which can preferably be observed with a distal-side picture sensor on the endoscopic instrument. In particular this makes sense with interstitial PDT, if for example the path to the tumour for example through natural body openings, such as the gut, ureter, oesophagus or windpipe can be shortened by way of an endoscopic instrument. The light applicator however can also be used completely without an endoscopic instrument, for example for percutaneous PDT, concerning which the insertion section is pierced from the outside through the skin up to the pathological tissue in a manner assisted by CT or ultrasound. The insertion section can preferably comprise one or more abstract or specific lateral length markings which informs the user of a relative or absolute piercing depth on piercing.

Optionally, the radial thermal insulation in the insertion section can reduce proximally in steps and/or in a continuous manner. Given a stepwise proximal reduction of the thermal insulation, the insertion section preferably has two or more steps of thermal insulation which are arranged distally of the proximal end of the insertion section. The radial thermal insulation, i.e. the thermal resistance $$R_{th} = \frac{\Delta T}{\dot{Q}}$$

in the radial direction, which determines the temperature different dT which effects a heat flow $$\dot{Q} = \frac{dQ}{dt}$$

in the radial direction, is determined by the thickness and the thermal conductivity of the material of the thermal insulation. The thermal insulation can be formed from one or more thermal insulation layers, wherein a plurality of thermal insulation layers can be formed from the same or different materials with different thermal conductivities. Given a circular cross section of the insertion section, the thermal resistance $$R_{th} = \frac{\Delta T}{\dot{Q}}$$

of a thermal insulation layer in the radial direction can be represented approximately by the following formula:

$$R_{th} = \frac{\ln\left(\frac{r_a}{r_i}\right)}{2\pi\lambda L},$$

where $r_a$ is the outer radius of the thermal insulation layer, $r_i$ the inner radius of the thermal insulation layer, L the length of the thermal insulation layer in the longitudinal direction of the insertion section and $\lambda$ the thermal conductivity of the thermal insulation layer. For a thermal insulation layer of PET, the thermal conductivity can be below 0.3 W/(Km) at 20° C. Given a plurality of thermal insulation layers, the individual contributions $R_{th}$ of each thermal insulation layer can be added into the total thermal insulation.

Where $r_a$ is the outer radius of the thermal insulation layer, $r_i$ the inner radius of the thermal insulation layer, L the length of the thermal insulation layer in the longitudinal direction of the insertion section and λ the thermal conductivity of the thermal insulation layer. For a thermal insulation layer of PET, the thermal conductivity can be below 0.3 W/(Km) at 20° C. Given a plurality of thermal insulation layers, the individual contributions $R_{th}$ of each thermal insulation layer can be added into the total thermal insulation.

The radial thermal insulation in the insertion section, i.e. the thermal resistance $$R_{th} = \frac{\Delta T}{\dot{Q}}$$

in the radial direction, at the LED is preferably at least twice as high as distanced by tenfold the light applicator diameter at the LED in the proximal direction away from the LED. The thermal insulation can be reduced to less than a third when distanced to the LED in the proximal direction by twenty-fold the light applicator diameter at the LED, compared to the radial thermal insulation at the LED. If therefore the light applicator diameter at the LED is 1 mm, then the radial thermal insulation at a distance of 1 cm to the LED in the proximal direction would only then be maximally half as great as at the LED. At a distance of 2 cm to the LED in the proximal direction, the radial thermal insulation would then yet only be at the most 33% of the radial thermal insulation at the LED.

Optionally, the light applicator in the insertion section can comprise at least one radial thermal insulation layer, wherein the total thickness of the at least one thermal insulation layer reduces proximally. Herein, the total thickness of the at least one thermal insulation layer can reduce proximally and/or their number. Additionally or alternatively to this, the thermal conductivity of the material of the thermal insulation can increase proximally, i.e. different thermal insulation materials can be arranged in the longitudinal direction of the insertion section.

Optionally, the diameter of the first lead can increase to the extent that the radial thermal insulation decreases proximally. In particular, this is advantageous if the total thickness of the at least one thermal insulation layer reduces proximally and the cross-sectional area of the light applicator is essentially constant over the length of the insertion section. The first lead can therefore be configured accordingly more thickly where the thermal insulation is thinner, in order to reduce the thermal resistance of the first lead in the proximal direction, such resistance behaviour being reciprocal to the cross-sectional area of the first lead.

Optionally, the thermal conductivity of the material of the radial thermal insulation can increase proximally in the insertion section. Thus different materials which are distributed over the insertion section in the longitudinal direction can form the thermal insulation and/or certain thermal insulation layers can extend over only certain length sections of the insertion section.

Optionally, the electrical lead which is necessary for the electricity supply of the LED can be used to stiffen the insertion section of the light applicator into a needle section, by way of it being configured in a rigid manner. The distal end section of the light applicator is herewith itself a relatively flexurally rigid needle with a much greater possible penetration depth compared to a laser fibre optic, without it bending under the resistance of the tissue on piercing. In this disclosure what is meant by bending stiffness is also a torsion stiffness. This means that not only does the needle bend to a lesser extent, buts also twists to a lesser extent.

Optionally, the light applicator can further comprise a second electrical lead for closing an electrical circuit for the supply of electricity to the LED, wherein the second lead is configured more thinly in the insertion section than the first lead in a manner such that the cross-sectional area of the second lead in the insertion section is less than 10% of the cross-sectional area of the light applicator. Optionally, herein the second electrical lead in the insertion section can be led along a side of the first lead in a manner in which it is electrically isolated from this and in the form of a flat flexible circuit board or as simple thin enamelled wire.

Optionally, the LED is arranged at a distal face side of the first lead, so that the main irradiation direction of the LED runs distally in the longitudinal direction of the light applicator. The LED is preferably in electrically conductive as well as thermally connective contact with the first distal face side of the first lead.

Optionally, the insertion section can be releasably connectable to a cable section at the proximal side or be fixedly connected to one another, for the supply of electricity. For the modular production, it can be advantageous if the insertion section and the cable section are releasably connectable to one another if the needle section depending on the application case must meet other demands, whereas the cable section can be configured equally for several application cases. Furthermore, a needle section, from which the cable section was separated or to which it has not yet been connected can simplify the handling of the needle section given the procedure of the placing of the needle section in the tissue. A fixed connection can be advantageous if for example identification means, such as for instance a mechanical or digital plug-in recognition which permits an automatic identification of the light applicator are provided in the cable section.

Optionally, the first lead can comprise a core with a first material and a jacket with a second material, wherein the first material is more thermally conductive than the second material and the second material is more flexurally rigid than the first material. The first material can comprise for example copper, aluminium or silver and the second material steel or another alloy with a comparative high modulus of elasticity. With this preferred embodiment, a high bending stiffness is achieved for the needle section with a comparatively hard jacket material, e.g. steel, given a low as possible material expense. The core of the more thermally conductive material, e.g. copper, aluminium or silver can herewith make up a large as possible cross-sectional share of the first lead, without significantly compromising the bending stiffness. Herewith a good compromise is achieved between the bending stiffness and the proximalward thermal conductivity. Preferably, the thermal conductivity of the core is at least fourfold the thermal conductivity of the jacket. The thermal conductivity of copper and silver as a core can be for example more than 400 W/(Km) at 20° C., that of aluminium more than 200 W/(Km), whereas the thermal conductivity of steel as a jacket lies significantly below 100 W/(Km), usually in the region of 50 W/(Km) at 20° C.

Optionally, the cross-sectional area of the core can be more than 40% of the cross-sectional area of the first lead.

Preferably, the core has a large as possible cross-sectional share of the first lead, in order to be able to lead away as much heat as possible proximally away from the LED. The cross-sectional share of the jacket is as small as possible, but large enough in order to achieve a sufficient bending stiffness. The jacket can have a thickness for example of about 50 μm to 300 μm, whereas the core can have a diameter of about 1 mm.

Optionally, the cross-sectional area of the core can be 0.8 to 1.2 times the cross-sectional area of the LED. The design freedom of designing the light applicator as thinly and here as minimal-invasively as possible can be limited by the lateral width and shape of the smallest possible LEDs which are available on the market at present or which can be manufactured. It is therefore advantageous to adapt the diameter of the first lead or its core essentially to the lateral width of the LED. The LED can then release heat proximally over its entire cross-sectional area to the first lead or its core in a particularly effective manner without having to unnecessarily thicken the light applicator as a whole. The cross-sectional shape of the first lead and/or its core can likewise be adapted the cross-sectional shape of the LED. For example, given a rectangular or square cross-sectional shape of the LED, the first lead and/or its core can also have a correspondingly rectangular or square cross-sectional shape.

Optionally, the cross-sectional area of the first lead can be at least as large as the cross-sectional area of the LED. The thin and flexurally rigid jacket can herein laterally encase the LED, thus project somewhat distally beyond the core in a sleeve-like manner. The first lead can comprise for example a round cross-sectional shape with a diameter which corresponds at least to the cross-sectional diagonal of a rectangular or square LED.

Optionally, the core with the first material with a high thermal conductivity can be used as a forward lead and the jacket with the second material with a high modulus of elasticity as a return lead or vice versa. Herein, the core and the jacket can be electrically isolated with respect to one another by way of a thin, electrically non-conductive layer which can be arranged between the two components. This has the advantage that one can make do without a separately configured second electrical lead, i.e. a second electrical lead which is configured as an additional component, in the region of the needle section, which in an advantageous manner can reduce the diameter of the needle section as that part which is inserted into the body.

Optionally the insertion section can comprise a needle tip which is arranged at least partly distally of the LED and which tapers distally, with a light-transparent scatter body for scattering the light of the LED. Preferably, the needle tip comprises a sleeve-like proximal section which laterally surrounds the LED and preferably a distal part of the first lead and at least partly forms a radial thermal insulation at the LED. The light-transparent scatter body and the sleeve-like proximal section can be formed for example essentially as one piece of plastic, for example of epoxy resin, wherein the epoxy resin can have a thermal conductively of for example below 2 W/(Km) at 20° C. The sleeve-like proximal section of the needle tip in turn can be completely or partly surrounded by one or more thermally insulating layers. The sleeve-like proximal section of the needle tip can serve for the secure fasting of the needle tip on the first lead of the insertion section.

Optionally, an additional improvement of the fastening reliability can be achieved by way of the first lead at the outside comprising at least one deepening or widening, for example as a local cross-sectional tapering or enlargement. By way of this, one succeeds in the sleeve-like proximal section of the needle tip being able to form a positive fit with the first lead. The needle tip can be configured as a plastic cast part or as a plastic injection moulded part which for example by way of peripheral injection or peripheral casting can form a positive fit with the outer-side deepening or widening of the lead by way of an undercut.

Optionally the volume of the needle tip is formed essentially by the scatter body and in a pointed and/or edge-like needle tip end region comprises a reinforcement element. This is particularly advantageous in order to provide a sharp and herewith minimal invasive as possible light-transparent needle tip which is reliable as well as inexpensive. The material of this reinforcement element can preferably on the one hand have a high strength and on the other hand a high toughness. The high strength is advantageous for sharp and accordingly thin but despite this highly loadable edges and/or points. The high toughness is advantageous in order, given a potential overloading of the sharp edges and/or tips, to avoid a breakage of edge/tip parts. In particular, this represents a problem with materials of a high brittleness, such as for instance glass. A material type which can unify both characteristics, i.e. high strength and high toughness, in particular is metal. If a brittle glass were to be used, then the needle tip end region would not be secure against a breakage given loading. A transparent plastic such as epoxy resin is not hard enough, thus too pliable, in order to design it in a sharp enough manner in the region of the needle tip end region, thus would bend given a loading in the needle tip end region. By way of the reinforcement element, the needle tip end region can be reinforced such that an inexpensively manufacturable transparent plastic such as epoxy resin can be used as a base material for the scatter body of the needle tip. Since such a plastic can be cast, injection moulded or processed in a comparable other form in a relatively simple manner, in contrast to glass, crystal etc. it is also possible to achieve the aforedescribed positive fit for improving the fastening reliability of the needle tip on the applicator by way of the needle tip being formed for example by way of peripherally injecting or peripherally casting the LED and a distal section of the first lead.

Optionally, the scatter body can be formed essentially of a light-transparent plastic with light-scattering particles and the reinforcement element of metal, for example steel. The share of the cross-sectional area of the needle tip which is assumed by the reinforcement element which is not transparent to light can be negligibly small, e.g. below 15%.

Optionally, the reinforcement element can be configured as a spike which is embedded at least partly into the scatter body or as a blade which is embedded at least partly into the scatter body. The respectively preferred embodiment can be dependent on the application. Given a percutaneous PDT on a prostate carcinoma, it can be the case for example that the light applicator passes healthy nerve paths or other sensitive vessels which should not be damaged or severed, on the way to the prostrate carcinoma. A spike-like design of the reinforcing element can then significantly reduce the risk of an unwanted injury to healthy tissue, nerves or vessels. Given a percutaneous PDT on a mammary carcinoma, in contrast the injury or severing of healthy fat tissue of could be less problematic and a blade-like design of the reinforcement element could reduce the resistance on piercing, reduce the scar formation and improve the healing process.

Optionally, the reinforcement element can project at least partly and/or laterally out of the scatter body. The reinforcement element then mainly acts as a piercing needle or piecing blade and to a lesser extent the needle tip end region of the scatter body itself, into which region it is at least partly embedded. The metallic reinforcement element can then be configured in a very pointed and/or sharp manner at the distal side, as a scalpel.

Optionally, the reinforcement element in the radial middle of the scatter body can project out of the scatter body further distally than at the radial outer region of the scatter body. Herewith, in particular given a blade-like embodiment, a central point can be achieved, from which point the blade sections extend obliquely in the radial-proximal direction, in order on piercing in the light applicator to achieve a good cutting effect without a lateral drifting away. Furthermore, such a measure reduces the force which is to be mustered by the user on inserting and advancing the applicator into the tissue.

Optionally, the reinforcement element at the lateral side can comprise a mirroring surface. By way of this, the compromising of the light irradiation by the reinforcement element which is not transparent to light, which is low in any case, can yet be further reduced.

Optionally, the scatter body in a first longitudinal section plane can taper distally at a first angle and in a second longitudinal section plane which lies perpendicularly to the first longitudinal section plane can taper distally at a second angle, wherein the second angle is more acute than the first angle. In the first longitudinal section plane, for example the skin and tissue can be cut, whereas the piecing opening in the second longitudinal section plane is merely widened by the scatter body. This is encouraged by obtuse edge angles in the second longitudinal section plane. This can improve the healing process and reduce scar formation. Optionally, herein the reinforcement element can be arranged in the first longitudinal section plane and reinforce the edge-like needle tip end region which runs therein. If the edge of the reinforcement element is configured in an accordingly sharp manner, this additionally favours the cutting effect in the first longitudinal section plane.

Optionally, the scatter body can be polyhedral with a first scatter body section, a second scatter body section which is arranged distally of the first scatter body section and a third scatter body section which is arranged distally of the second scatter body section, wherein the first scatter body section has an essentially square cross section, wherein the second scatter body section has an essentially octagonal cross section and wherein the third scatter body section has an essentially rhombic cross section. On piercing-in the distal-side third scatter body section, the essentially rhombic piecing opening widens in the direction of both rhomboid diagonals, wherein preferably the reinforcing element cuts open the piercing opening along the longer rhomboid diagonal. As soon as the second middle scatter body section reaches the piercing opening, the maximal opening along the longer rhomboid diagonal has already been reached and the piercing opening is widened with the octagonal cross section perpendicularly to the section plane of the reinforcing element. Since preferably all angles of those edges which do not contain the reinforcement element are blunt, essentially it is only a stretching/widening of the tissue and no cut which takes place in the direction perpendicular to the plane with the reinforcement element. The proximal first scatter body section then has the essentially square cross section of the insertion section, so that the piercing opening has then reached the maximal size for inserting the insertion section. It has been found that the healing of a piercing opening which is formed in such a manner entails less scar formation.

Optionally, the reinforcement element can be configured as two blades which in cross section are arranged in a crossed manner to one another. This embodiment can be particularly advantageous for particularly firm tissue which is stretchable to a lesser extent and heals to an improved extent if it is cut in a crossed manner than if it were stretched.

The terms "distally" or "proximally" are here to mean a relative position which is located distally and proximally respectively of a user of the system as a reference position. The terms "distal-side" and "proximal side" herein accordingly mean a position at the distal side and proximal side respectively of an object. The terms "distalward" and "proximalward" herein mean a respective direction which extends distally and proximally respectively.

BRIEF DESCRIPTION OF THE DRAWINGS

In the drawings:

FIG. 7 is a schematic representation of a further exemplary embodiment of a light applicator disclosed herein;

FIG. 8 is a schematic representation of a further exemplary embodiment of a light applicator disclosed herein;

FIG. 11a, 11b, 11c and 11d are schematic representations of an insertion section of four further exemplary embodiments of a light applicator disclosed herein;

FIGS. 12a, 12b and 12c schematic representations of the distal tip of a possible light applicator of an exemplary embodiment of the light applicator system disclosed herein;

FIG. 13 is a schematic representation of the distal tip of a possible light applicator of an exemplary embodiment of the light applicator system disclosed herein, during the operation;

FIG. 14 is a schematic representation of the distal tip of a possible light applicator of an exemplary embodiment of the light applicator system disclosed herein, with two different detail variants;

FIG. 15 is a schematic representation of the distal tip of a possible light applicator of another exemplary embodiment of the light applicator system disclosed herein, with four different detail variants;

FIG. 16 is a schematic representation of the distal tip of a possible light applicator of an exemplary embodiment of the light applicator system which is disclosed herein, on piercing the skin of a patient;

FIG. 17 is a schematic representation of the distal tip of a possible light applicator of another exemplary embodiment of the light applicator system disclosed herein, on piercing the skin of a patient;

FIG. 18 is a schematic representation of the distal tip of a possible light applicator of another exemplary embodiment of the light applicator system disclosed herein, on piercing the skin of patient;

FIG. 19 is a schematic cross section of the distal tip of a possible light applicator of an exemplary embodiment of the light applicator system disclosed herein, with two different detail variants;

FIG. 20 is a schematic representation of a reinforcement element of a distal tip of a possible light applicator of an exemplary embodiment of the light applicator system disclosed herein, with three different detail variants;

FIG. 22 is a schematic cross section of the distal tip of a possible light applicator of an exemplary embodiment of the light applicator system disclosed herein, with three different detail variants;

FIG. 23 is a schematic representation of a reinforcement element of a distal tip of a possible light applicator of an exemplary embodiment of the light applicator system disclosed herein;

FIG. 24 is a schematic representation of the distal tip of a possible light applicator of another exemplary embodiment of the light applicator system disclosed herein, with a skin opening on piercing, in five different phases;

FIG. 25 is a schematic representation of the distal tip of a possible light applicator of another exemplary embodiment of the light applicator system disclosed herein, with two different detail variants;

FIG. 26 is a schematic representation of the distal tip of a possible light applicator of another exemplary embodiment of the light applicator system disclosed herein, with two different detail variants.

DESCRIPTION OF PREFERRED EMBODIMENTS

Figure 1:
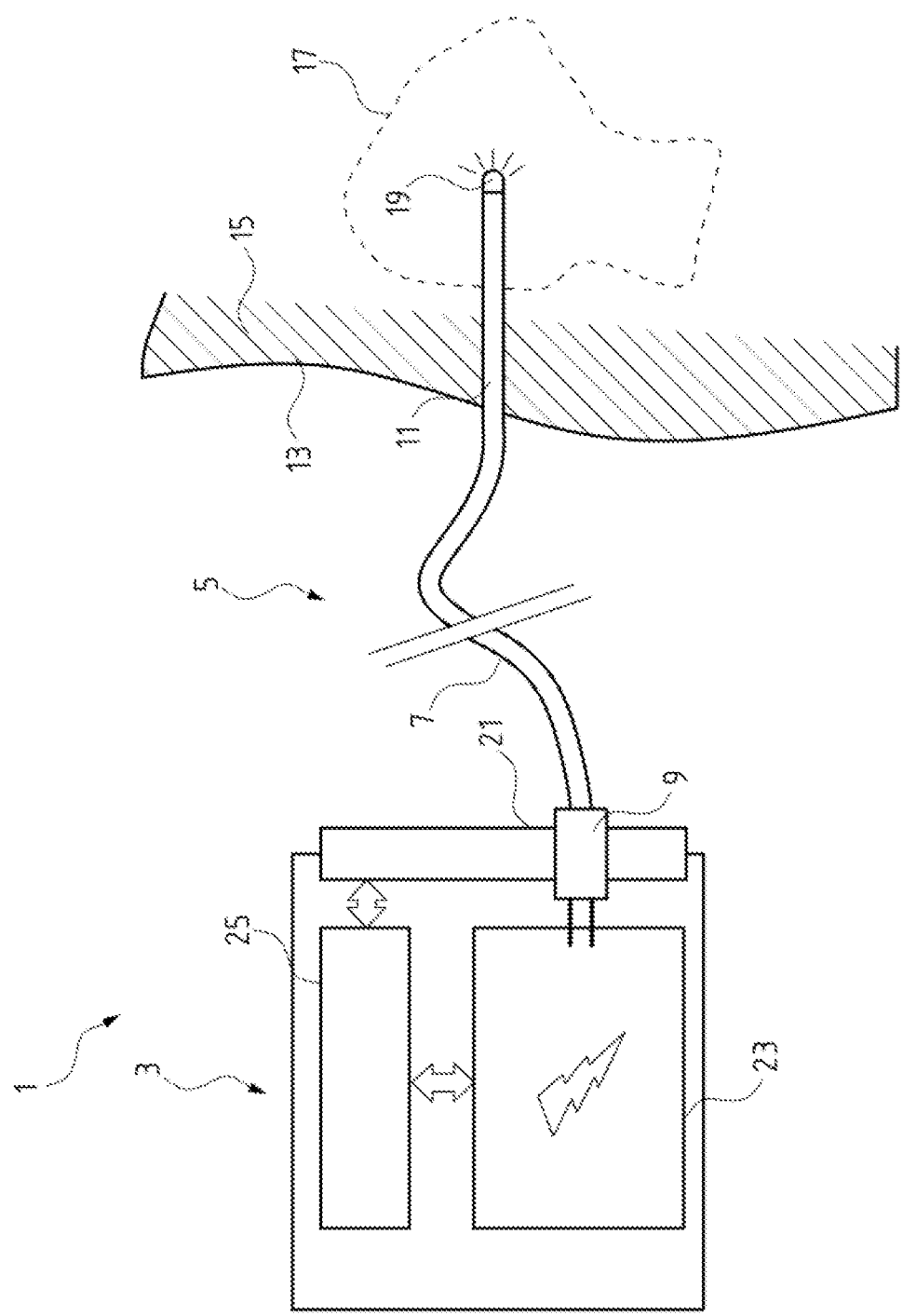
FIG. 1 is a schematic representation of an exemplary embodiment of a light applicator system disclosed herein.

FIG. 1 shows a light applicator system 1 with a light applicator operation unit 3 and an exchangeable light applicator 5. The light applicator 5 consists essentially of a flexible cable section 7 which extends from a proximal-side plug 9 to a distal-side insertion section 11. The insertion section 11 in contrast to the cable section 7 is the section of the light applicator 5 which is envisaged to be pierced into organic tissue of a body 13. The light applicator 5 here is suitable for percutaneous PDT and is shown in PDT operation. The insertion section 11 here is configured as a rigid needle section which for example assisted by CD or ultrasound from the outside and with the distal tip is pierced through the skin 13 of a patient and underlying healthy tissue 15 into pathological body tissue 17, e.g. a malignant tumour.

At the distal tip, the insertion or needle section 11 comprises a distal-side LED 19 for in-situ generation of excitation light for the PDT. If for example Chlorin e6 is used as a sensibiliser for PDT, then the LED 19 which is especially configured for this can emit excitation light as isotropically as possible in the wavelength range of 660-670 nm. Chlorin e6 which as a sensibiliser has selectively accumulated previously in the pathological body tissue 17, on account of the effect of light produces oxygen radicals which destroy the pathological body tissue 17. Since Chlorin e6 does not accumulate in healthy tissue, the healthy tissue 15 remains essentially uninfluenced by the light.

The LED is supplied with electricity from the light applicator operation unit 3 via an electrical lead in the cable section 7 and insertion section 11. For this, the proximal-side plug 9 of the light applicator 5 is inserted into a terminal 21 on the light applicator operation unit 3. For the electricity supply of the light applicator 5, the light applicator operation unit 3 comprises an electrical supply module 23 which is configured to provide a certain operating current for the connectable light applicator 5 at the terminal 21. Furthermore, the light applicator operation unit 3 comprises a control module 25 which configured to identify the plug 9 and to instruct the supply module 23 into providing a respective operating current.

The terminal 21 can for example be a plug-in strip with a plurality of plug points, wherein only certain plug shapes fit certain plug-in points, as an identification means in the form of a mechanical recognition, so that given an inserted plug 9, it is unambiguously determined which type of light applicator 5 is located at a plug-in point. The control module 25 can then provide set operating parameters (current, voltage, operation, duration, etc.) per plug-in point. Alternatively or additionally, the applicator type can be stored in the plug 9 as an identification means in the form of signal-based recognition in a manner in which it can be read out by the control module 25 and the supply module 23 activated accordingly. Given a signal-based recognition, the light applicator 5 can "notify" and actively identify itself at the control module 25 and/or be passively enquired by the control module 25. A prior use of the light applicator 5 can also be stored in the control module 25 and/or in the plug 9, so that only a one-off use of the light applicator 5 can be permitted.

Figure 2:
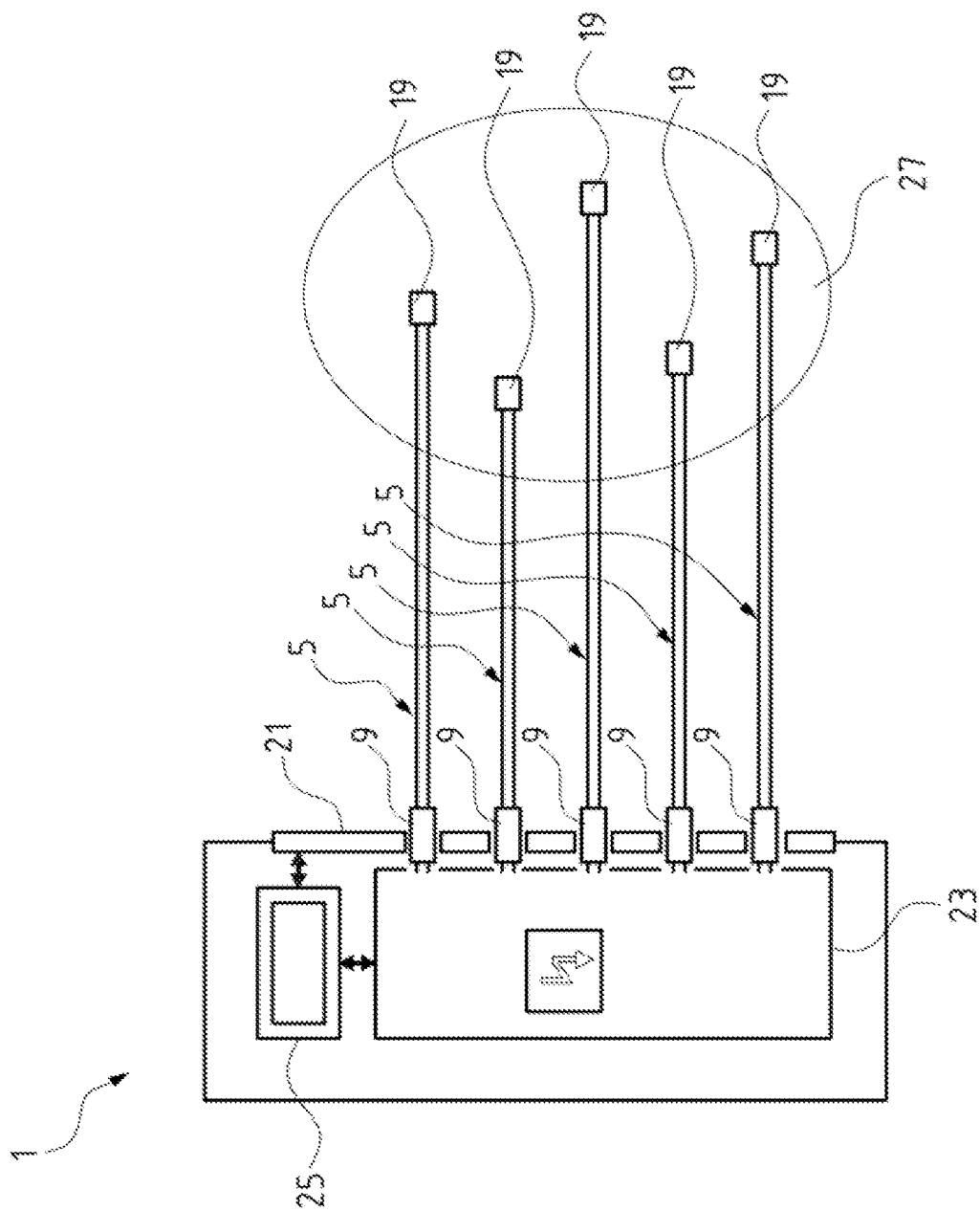
FIG. 2 is a schematic representation of another exemplary embodiment of a light applicator system disclosed herein.

In FIG. 2, the light applicator system 1 comprises a plurality of light applicators 5 which at the same time are connected to a plurality of terminals 21, in order to be commonly used for a PDT of a complete organ 27. The light applicators 5 can also be of the same type or at least partly different type. The light applicators 5 are pierced through the skin at different locations and distributed at different piercing depths into the organ 27, so that the LEDs 19 illuminate the organ with excitation light as homogeneously as possible. Above all, this makes since with large tumours and/or ones which cannot be precisely localised. Since healthy tissue suffers no injury due to the PDT, it is useful to illuminate a volume or a complete organ around the tumour in a generous manner, in order to reduce the risk of pathological tissue remaining untreated. The individual light applicators 5 can be fixed with a certain type, at a defined position, at a defined piercing angle and depth, for example by way of a template or jig which is bonded onto the skin or fixed in another manner. The respective assignment of the light applicators 5 to the terminals 21 however can be specified via the identification means, so that for a specified type of PDT on a certain organ 27, automatically the correct operating parameters are provided at each terminal 21 by the control module 25. The risk of error given a complex setting of a plurality of light applicators 5 can herewith be reduced.

Figure 3:
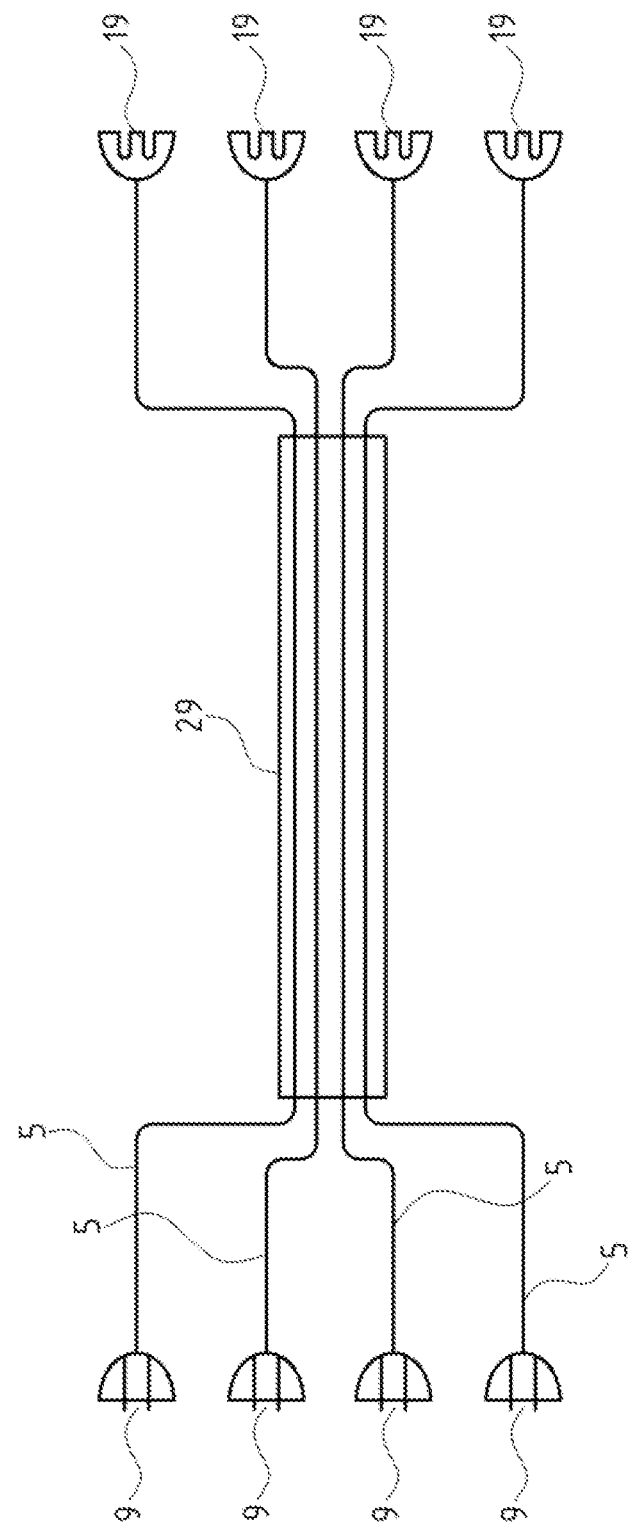
FIG. 3 is a schematic representation of an example of a light applicator of an exemplary embodiment of a light applicator system disclosed herein.

In FIG. 3 it is schematically shown that a plurality of light applicators 5 for interstitial or percutaneous PDT can be bundled at least in sections in the flexible cable section 7, for example in the form of a multi-core flat band cable 29. The light applicators 5 however can also be led through one or more working channels of an endoscope or trocar in a bundled manner or individually.

Figure 4:
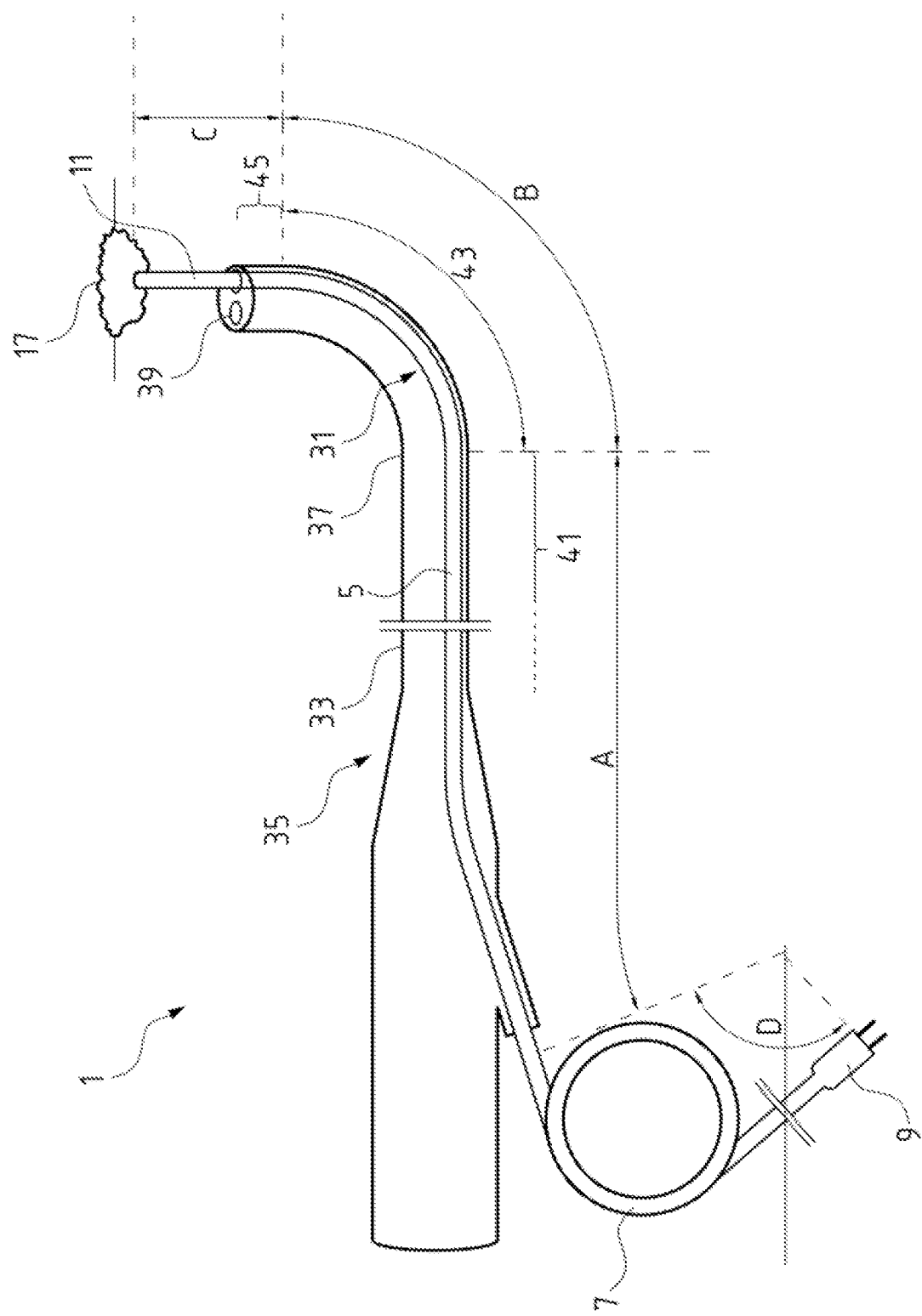
FIG. 4 is a schematic representation of another example of a light applicator of an exemplary embodiment of a light applicator system disclosed herein.

An embodiment of a light applicator system 1 is shown in FIG. 4, concerning which a light applicator 5 for interstitial PDT is led through a working channel 31 in the shank 33 of a shank instrument 35 in the form of an endoscope. The shank 33 comprises an insertion section 37 which is envisaged for being inserted into the body of a patient. Optionally, a picture sensor 39 can be arranged at the distal end of the insertion section 37, in order to be able to take a picture of the inside of the body of the patient. The insertion section 37 comprises a first shank section 41, a second shank section 43 and a third shank section 45, wherein the first shank section runs proximally of the second shank section 43 and the third shank section 45 distally of the second shank section 43. The shank 33 can be bent in the second shank section 43 and/or is less flexurally rigid than the first and/or the third shank section 41, 45. Herewith, the distal end of the insertion section 37 can be placed at contorted regions of the interior of the body, such as for instance renal calices or greatly branched respiratory passages, in a minimal invasive manner.

Corresponding to the shank sections 41, 43, 45, the light applicator 5 also comprises different light applicator sections, specifically a first light applicator section A, a second light applicator section B and a third light applicator section C, wherein the first light applicator section A runs proximally of the section light applicator section B and the third light applicator section C distally of the second light applicator section B. The second light applicator section B is less flexurally rigid than the first A or and/or third light applicator section C. The second light applicator section B is arranged at least partly in the second shank section 43 when the distal-side LED 19 of the light applicator 5 is positioned at the distal end of the insertion section. The light applicator sections A, B, C are therefore matched in length to the shank 33 of the endoscope 35, so that on the one hand the light applicator 5 is configured there in a sufficiently flexurally rigid and torsionally rigid manner, in order to be able to control the distal end of the light applicator 5 and one the other hand is configured flexible enough in order to compromise the bendability of the shank in the second shank section 43 as little as possible. In this embodiment example, the light applicator 5 yet has an optional fourth light applicator section D in the proximal flexible cable section 7 which runs at the proximal side from the first light applicator section A and in a manner in which it can be wound about a certain radius outside the endoscope 35. The distal insertion section 11 of the light applicator 5 can project out at the distal end of the working channel 31 and be pierced into pathological tissue 17 for interstitial PDT. For this, the distal insertion section 11 of the light applicator 5 can be flexible or as a needle section be relatively flexurally rigid. A flexurally rigid needle section 11 can increase the penetration depth into the tissue, whereas a flexible insertion section 11 can be pushed or pulled through an angled working channel 31 to a better extent.

Figure 5:
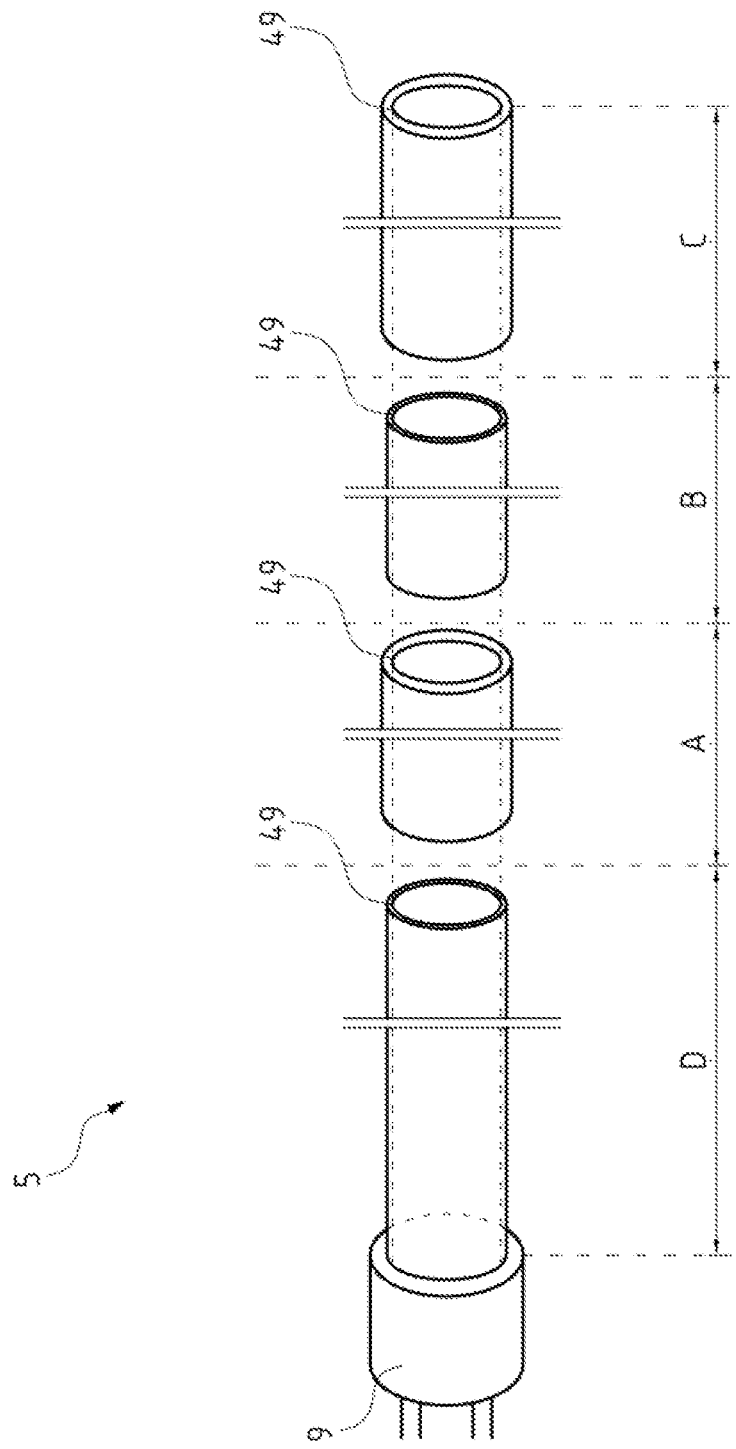
FIG. 5 is a schematic representation of a further exemplary embodiment of a light applicator system disclosed herein.

As is shown in FIG. 5, the light applicator 5 in the second light applicator section B is configured more thinly than in the light applicator sections A and C, since a lower bending stiffness and torsion stiffness is needed for small angle radii. It is thicker in the light applicator sections A and C, where a greater bending stiffness and torsion stiffness is advantageous for the handling. Herein, the radial extension of the electrical lead itself and/or its insulating encasing can be adapted to the requirements for the locally bending stiffness and torsion stiffness. Herein, the light applicator 5 does not to be differently thick in the different light applicator sections A-D as a whole, but for example only a stiffening jacket differently thick in the different light applicator sections A-D. A very simple solution is to design a radial encasing 49 as an electrical insulator and/or thermal insulation in sections as flexible tubes with a different wall thickness and/or in a different number as at least partly overlapping flexible tubes and herewith achieving different bending and torsional stiffnesses in the light applicator sections A-D. The flexible tubes can herein be configured as shrink tubes. The wall thickness of the encasing can be configured in a comparatively thin manner, since the increase of the bending stiffness which is effected by the encasing correlates to the areal moment of inertia $I_r$. For example given an annulus as a cross-sectional shape of the encasing, it is the case that $$I_r = \frac{\pi}{4}(R^4 - r^4),$$

so that the bending stiffness scales with the fourth power of the radius, wherein R is the outer radius of the encasing and r the inner radius of the encasing. For an encasing cross section with a square box profile with an outer width A and an inner width a, accordingly $$I_r = \frac{1}{12}(A^4 - a^4).$$

Even the slightest differences of the thickness of the encasing between the light applicator sections A to D in the region of 10 µm can therefore effect a significant influence on the bending stiffness and torsion stiffness.

Figure 6:
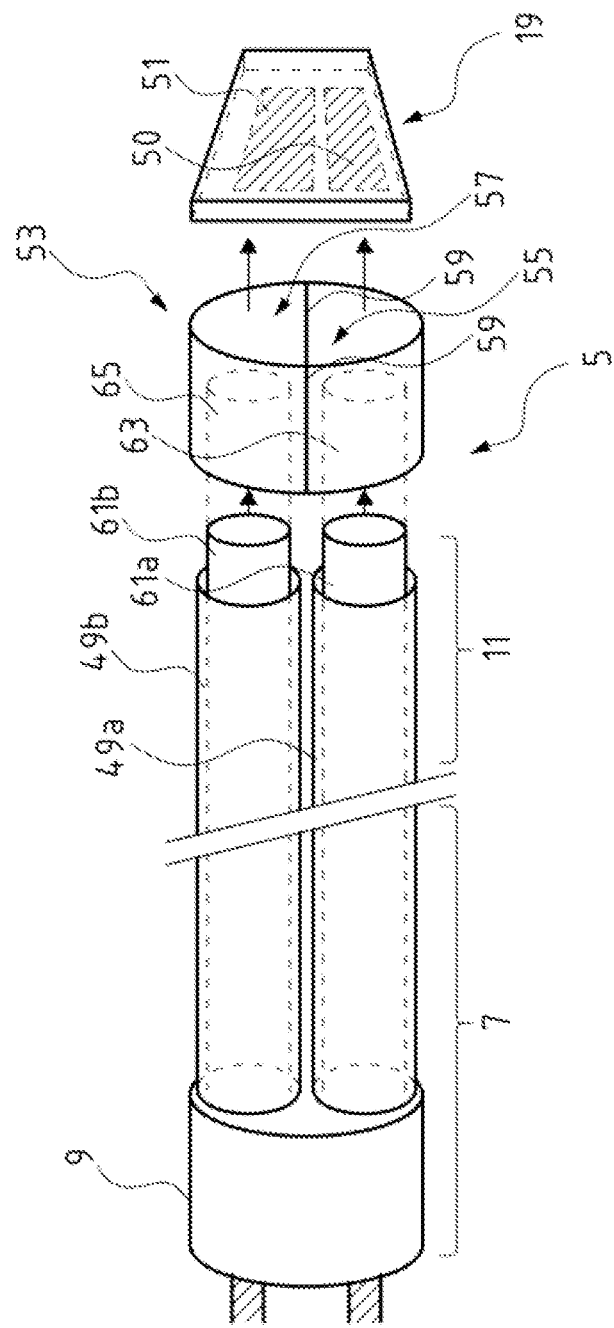
FIG. 6 is a schematic representation of a further exemplary embodiment of a light applicator disclosed herein.

FIG. 6 shows an embodiment of the light applicator 5, concerning which a so-called flip-chip is applied as an LED 19, concerning which the first electrical contact 50 (here anode contact) as well as the second electrical contact 51 (here cathode contact) are arranged at the proximal side. The LED chip 19 here for example with a thin conductor adhesive layer (not shown) is bonded onto an adapter piece 53 which with regard to its lateral dimensions is configured such at a large-surfaced contact of the LED chip 19 is rendered possible and herewith a good proximal flow of heat from the LED 19 to the adapter piece 53. Herein, the adapter piece 53 as in FIG. 6 can be configured of two metal halves 55, 57 which are each in electrically conductive contact with the contacts 50, 51 of the LED and are electrically isolated with respect to one another by way of a thin isolator layer 59. Alternatively, the adapter piece 53 can be configured for example as a single-piece ceramic piece with metallic feedthroughs. The LED is supplied with electricity over the length of the light applicator 5 with an electrical lead 61, wherein here the electrical lead 61 is configured as twin strands 61*a,b*, wherein one of the twin strands 61*a,b* serves for the feeding of current and the other of the twin strands 61*a,b* for leading away the current. The adapter piece 53 at the proximal side comprises contact receivers 63, 65, to which the distal end of the electrical lead 61 is connectable in an electrically conductive manner. The electrical lead 61 can be configured in a flexible or rigid manner at least in sections. Whether flexible or rigid, at all events it is advantageous for the proximal dissipation of heat if the electrical lead 61 has a large as possible cross-sectional share, e.g. at least 70% of the light applicator 5, since the electrical lead 61 is a better thermal conductor than an insulating encasing 49a,b which surrounds the electrical lead 61.

In contrast to the embodiment according to FIG. 6, a light applicator 5 is shown with an LED chip 19 in FIG. 7, said LED chip comprising a second electrical contact 51 which is large-surfaced at the proximal side and which simultaneously serves as a light reflector in the distal direction, and a distal first electrical contact which is relatively small-surfaced at the distal side. Here, the electrical lead 61 is configured as a coaxial cable, wherein its core 61a at the distal side is conductively connected to the proximal-side second electrical contact 51 of the LED 19 by way of conductive adhesive or solder. For a good as possible proximal dissipation of heat from the LED 19 via the core 61a, this core has a relatively large cross-sectional area share of the electrical lead 61 or of the complete light applicator 5, for example at least 70%. An outer lead 61b and an isolator layer 59 which is arranged between the outer lead 61b and the core 61a are accordingly each configured as thinly as possible. Towards the outside, the outer lead 61b is likewise surrounded by at least one as thin as possible, isolating encasing (not shown in FIG. 7). As is FIG. 5, in sections the bending stiffness of the light applicator 5 can be defined via the thickness and/or layer number of the encasing. The core 61a can be configured as a relatively rigid, solid wire or an as flexible strand bundle.

The outer lead 61b in FIG. 7 serves as a return lead which via a distal-side metallic sleeve 67 which is pushed over the LED 19 is electrically conductively connected to the first electrical contact 50 of the LED 19. A contact clip 69 of the sleeve 67 projects radially inwards for the electrical contact between the first electrical contact 50 and the sleeve 67. Even if not shown in all figures, concerning all embodiments a component which shapes a light beam is advantageously arranged advantageously distally of the LED, in order to achieve desired irradiation characteristics. For example, an isotropic irradiation can be desired for PDT, so that a scatter body 71 (see FIGS. 8-10 and 13-27) can form the component which shapes the light beam. In the case that a focussing of the light is desired, a lens as a component which shapes the light beam can be arranged distally of the LED chip 19.

An embodiment of the light applicator 5 which is particularly advantageous for percutaneous PDT is shown in FIG. 8. A plan view of the LED 19 is shown separately in FIG. 8 at the right. The proximal cable section 7 of the light applicator 5 with a proximal-side plug 9 for connection onto a light applicator operating unit 3 is flexible and at the distal side comprises a releasable connection terminal 73 for a relatively rigid distal needle section 11. The needle section 11 serves as a whole or partly as an insertion section for piecing into a tissue of a body. The needle section 11 obtains is bending stiffness mainly due to a central, solid, rigid, rod-like first electrical lead 61a. Analogously to FIG. 7, an LED 19 is connected at the distal side to the first electrical lead 61a. It is clear from the plan view upon the LED 19 at the right in FIG. 8 that the electrical lead 61 as the LED 19 has an essentially square cross section which is only a little larger than the LED 19. The cross section of the smallest possible LED 19 which at present is obtainable on the market today and can be produced here places a lower limit on the miniaturisation of the light applicator 5 which is configured as minimal-invasively as possible, thus thinly and hence is to project beyond the lateral dimensions of the LED 19 as little as possible. Hence at present light applicator cross sections of significantly less than 1 mm$^2$ can be achieved, for example 0.25 mm$^2$ and less.

A second electrical lead 61b as a return lead in the form of a very thin flex-circuit-board or an enamelled wire which is isolated with respect to the first electrical lead 61a can be led along a side of the first electrical lead 61a and be folded or bent in an L-shaped manner at its distal end, in order to contact the distal-side first electrical contact 50 of the LED 19. The metallic sleeve 67 of FIG. 7 can then be done away with in both cases. The leads 61a, 61b are here encased with a thin encasing 49 which is preferably configured in a biocompatible manner of plastic as a shrink tube and improves the sliding behaviour of the needle section 11 through the body tissue. Furthermore, the encasing 49 serves as an electrical insulation and thermal insulation to the outside.

A component which shapes a light beam and which is arranged distally of the LED 19 is shown in the form of a light-transparent scatter body 71 in FIG. 8 and functions as a distally tapering needle tip of the needle section 11. Advantageous designs of the needle tip are shown in more detail in FIGS. 12 to 27.

Figure 9B:
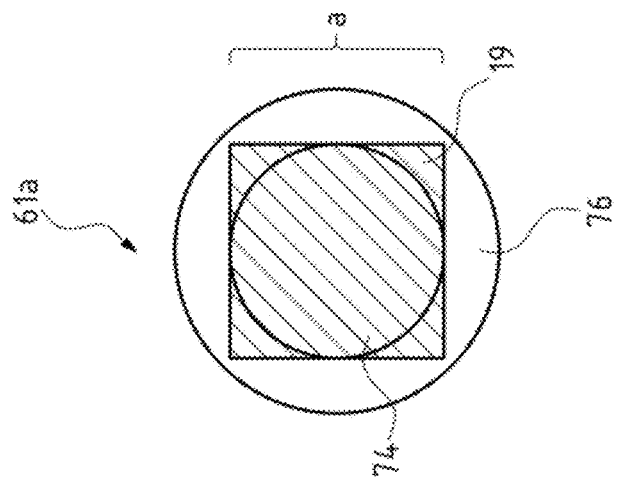
FIGS. 9a and 9b, are a schematic longitudinal section and a schematic plan view of a first lead with a distal-side LED of a possible light applicator of an exemplary embodiment of the light applicator system disclosed herein.
Figure 9A:
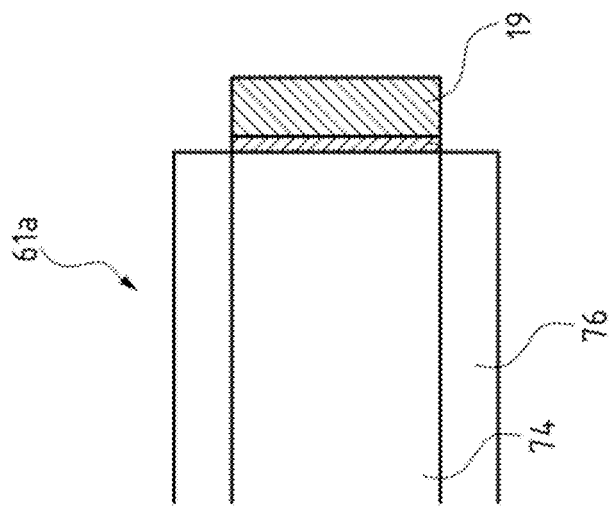
Figure 10B:
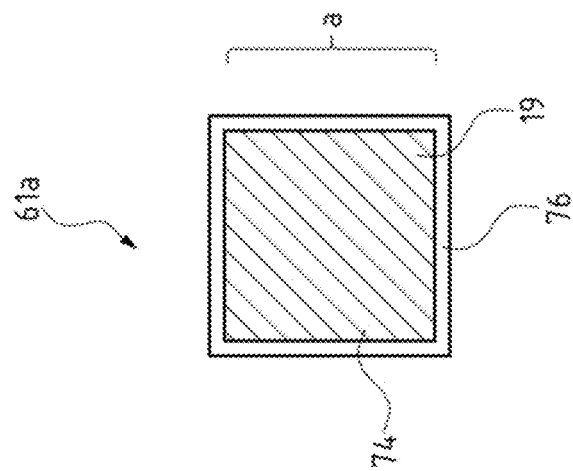
FIGS. 10a and 10b, are a schematic longitudinal section and a schematic plan view of a first lead with a distal-side LED of a possible light applicator of an exemplary other embodiment of the light applicator system disclosed herein.
Figure 10A:
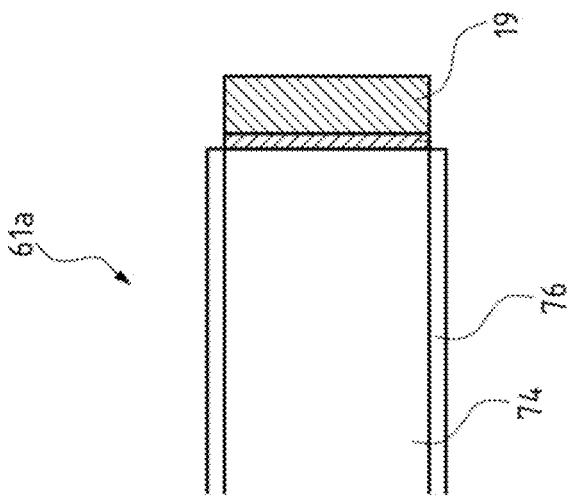

In order given cross sections below 1 mm$^2$ to achieve a high bending stiffness of the first electrical lead 61a, it is advantageous to use a material with a high as possible modulus of elasticity as a first electrical lead. For example, steel with above 200 MPa has a high modulus of elasticity. However, steel has the disadvantage that its thermal conductivity lies significantly below 100 W/(Km) at 20° C., usually in the region of 50 W/(Km) at 20° C. Since the first electrical lead 761a is not only flexurally rigid but is also to lead the waste heat of the LED in the proximal direction as well as possible, a first electrical lead 61a of copper or silver with a thermal conductivity of more than 400 W/(Km) at 20° C. would make sense for thermal conduction, or at least of aluminium with a thermal conductivity of more than 200 W/(Km) at 20° C. However copper, aluminium and silver at below 100 MPa have significantly lower modulus of elasticity than steel. For achieving a high flexural rigidity given a simultaneously high thermal conductivity, the electrical lead 61a as is shown in FIGS. 9a,b and FIG. 10a,b is configured with a copper core 74 and a steel jacket 76. The steel jacket 76 can be configured in a relatively thin-walled manner in comparison to the radius of the copper core 74, since the stiffening effect as described above scales with the fourth power of the radius. As the same time, the proximalward conduction of heat is better the larger the cross section of the copper core 74. For a good as possible thermal dissipation, the diameter of the copper core 74 is adapted to the lateral dimensions of the LED 19. In FIGS. 9a,b, the cross section of the lead 61 is round and the LED 19 roughly square with a side length a, so that the diameter of the copper core 74 is about a. The steel jacket 76 here is at least $(\sqrt{2}-1)$ a thick, so that the corners of the LED 19 do not project laterally beyond the lead 61. In FIGS. 10a,b, the cross section of the lead 61 as the LED 19 is roughly square, wherein the cross section of the copper core 74 corresponds roughly to the cross section of the LED 19. The steel jacket 76 here is significantly thinner than in FIGS. 9a,b, e.g. less than 0.15·α thick.

The thermal management in the insertion section 11 of the light applicator 5 is clear in FIGS. 11a and 11b. The insertion section 11 here can be configured in a rigid or flexible manner, thus the electrical lead 61 can be configured as solid rod or as a flexible strand bundle. Due to the released optical power that develops with an increasing LED temperature. it is a technical challenge, given small cross sections, in particular cross sections below 1 mm$^2$, to lead away the waste heat of the LED 19 so well that the LED 19 is not damaged and to maintain the magnitude of the released optical power even with an increasing switch-on time of the LED. On the other hand, the surrounding body tissue cannot be heated to such a high degree that it becomes injured. Too high a thermal insulation damages the LED 19 and too weak a thermal insulation, on account of an extremely inhomogeneous radial flow of heat and above all in the region of the LED 19 a very high greatly increased radial flow of heat from the applicator to the surrounding tissue, injures the tissue there. For solving this problem the radial thermal section reduces proximalward of the LED 19. In the shown embodiment examples, this is effected in a stepwise manner between several thermal insulation sections E, F, G. In a first distal thermal insulation section E which radially surrounds the LED 19, the radial thermal insulation is the greatest, so that in this region of the insertion section 11, thus in the region of the LED 19 as a heat source, where the heat flow dQ/dt in the light applicator 5 as a whole is very high since almost no heat could be dissipated to the external environment there, the radial heat flow dQ/dt from the light applicator 5 to the tissue is damped to a moderate amount by way of a good radial thermal insulation, in order not to damage the surrounding tissue. For this, the thermal insulation comprises three layers in the distal thermal insulation section E.

Radially at the very inside, a proximal section of the needle tip 71 which extends around the LED 19 in a sleeve-like manner acts as a first thermal insulation layer 75 in the first distal thermal insulation section E, wherein the needle tip distally of the LED 19 forms a light-transparent scatter body. The scatter body 71 effects an isotropic as possible irradiation of the light at a large as possible spatial angle. The first thermal insulation layer 75 as the scatter body 71 itself comprises a plastic, for example epoxy resin as a main constituent. Plastics are advantageously characterised by a comparatively low thermal conductivity. A first shrink tube 77 of plastic, for example polyethylene terephthalate (PET) as a second thermal insulation layer surrounds the first thermal insulation layer 75 in a distal thermal insulation section E. As a third thermal insulation layer, a second shrink tube 79 of plastic, for example polyethylene terephthalate (PET) surrounds the second thermal insulation layer 77 in the first distal thermal insulation section E.

A second thermal insulation section F which consists of the second thermal insulation layer 77 and of the third thermal insulation layer 79 extends proximally from the first distal thermal insulation section E. The first thermal insulation layer 75 of the proximal sleeve section of the needle tip 71 does not extend into the second thermal insulation section F. By way of this, the lead 61 can better radially dissipate the heat than in the first thermal insulation section E, so that a heat accumulation is avoided and a proximal heat dissipation from the LED 19 through the lead 61 remains ensured. A third thermal insulation section G which consists only of the third thermal insulation layer 79 extends proximally from the second distal thermal insulation section F. The second thermal insulation layer 77 does not extend into the third thermal insulation section G. By way of this, the lead 61 can radially dissipate the heat to an even better extent than in the second thermal insulation section F, so that here too, a heat accumulation is avoided and a proximalward heat dissipation from the LED 19 through the lead 61 remains ensured. As a result, the radial thermal insulation which reduces proximally from the LED 10 effects a distribution of the radial heat flow over the length of the insertion station 11, so that the longitudinal temperature gradient ΔT/ΔL at the outer radius of the third thermal insulation layer 79 over the thermal insulation sections E, F, G is as low as possible and thus temperature peaks which are injurious to tissue are avoided. As is indicated by the size of the white block arrows in FIG. 11a,b, the difference in the radial temperature gradient ΔT/Δr between the thermal insulation sections E, F, G is compensated as much as possible by the difference thickness of the radial thermal insulation and the different radial thermal resistances of the thermal insulation sections E, F, G which result from this, so that the thermal power dQ/dt which is s transmitted radially outwards through the thermal insulation sections E, F, G is as equal as possible.

The strength of the thermal insulation is determined predominantly over the total thickness of the thermal insulation in the FIGS. 11a and 11b. As is shown in FIG. 11a, the light applicator 5 can therefore be configured more thinly proximally. This however is not of huge advantage since the maximal cross section of the light applicator 5 is defined by the first thermal insulation layer with three thermal insulation layers. In FIG. 11b, it is shown that the cross section of the lead 61 can increase in manner corresponding to the proximally reducing thickness of the thermal insulation, so that the cross section of the light applicator 5 remains essentially constant over the thermal insulation sections E, F, G. Herewith, the proximalward thermal conductance dQ/dt through the lead 61 is accordingly improved.

It is shown in FIGS. 11c and 11d how an additional improvement of the fastening reliability for the needle tip 71 can be achieved. The lead 61 for this in a distal end section at the outer side comprises at least one depending 80 (see FIG. 11c) and/or widening 82 (see FIG. 11d) for example as a local cross-sectional tapering and/or cross-sectional enlargement. By way of this, one succeeds in the sleeve-like proximal section 75 of the needle tip 71 forming a positive fit with the first lead 61. The needle tip 71 can be configured as a plastic cast part or as a plastic injection moulded part which for example by way of peripheral moulding or peripheral casting can form a positive fit with the outer-side deepening 80 or widening 82 of the lead 61 by way of an undercut 84.

Different designs of the needle tip or scatter body 71 are shown in the FIGS. 12 to 27. FIGS. 12a-c each show a basic sleeve-like construction of a beam-shaping component distally of the LED (not shown). In FIG. 12, the needle tip is essentially pot-like with a plane end-face 81 and slightly rounded edges 83. The needle tip in FIG. 12a is therefore relatively blunt. This can be advantageous of no tissue is to be cut but merely pressed away. However, such a needle tip is less suitable for percutaneous PDT due to the high resistance of piercing. In FIG. 12b, the end-face 81 is completely rounded which on the one hand reduces the resistance on piercing compared to a plane end-face 81 of FIG. 12a and on the other hand achieves a lens effect. In FIG. 12c, the needle tip tapers distally in a cone-like manner into a relatively blunt tip 85. The cone volume here is largely filled out with a light-scattering material 87.

FIG. 13 shows a light applicator which is pierced percutaneously (through the skin 13) into pathological tissue 17, with a distal-side needle tip which is configured as a dome-like scatter body 71. The scatter body 71 scatters the light 89 which is emitted from the LED 19 according to emitting characteristics of a Lambert beamer, in a manner such that light 91 which leaves the scatter body 71 is irradiated as isotropically as possible at a large as possible spatial angle. The light which is irradiated from the scatter body 71 also to some extent has proximally directed direction components by way of this.

With interstitial or percutaneous PDT, the mechanical effect upon the skin 13 and tissue 15, 17, in particular healthy tissue 15 which must possibly be passed on the way to pathological tissue 17 must be as minimal-invasive as possible. First and foremost, one aims for the incision to cause no permanent injury to the skin 13 and healthy tissue 15. Furthermore, the incision should heal as quickly as possible and leave no or small as possible scars. For this purpose, it can be advantageous to design the tip of the light applicator 5 in a particularly pointed and sharp manner. Herein however, it can be technically difficult to be able to manufacture the distal tip and/or the edge sharply enough from the light-transparent material of the scatter body 71. For example, epoxy resin as most other plastics is relatively soft and on piercing can be bent at the tip and/or edge. Harder light-transparent material such for instance quartz glass, although being more flexurally rigid, the machining however requires significantly more effort and on account of this entails considerably greater costs. Moreover, harder transparent materials such as for example quartz glass are brittle, so that the risk of splintering away would be too high. For solving this problem, as is shown in FIG. 14, a needle tip end region 63 of the for example cone-like or pyramid-like scatter body 71 comprises a reinforcement element 96. The reinforcement element 95 is of hard metal, such as for instance steel, and is embedded at least partly into a relatively soft scatter body material such as for instance epoxy resin. In the embodiment example of FIG. 14, the reinforcement element 95 is configured as a relatively short spike which for reinforcement of the needle tip end region 93 for increasing the bending stiffness as well as the bending strength can be completely embedded (see detailed view at the top right in FIG. 14) or for sharpening the needle tip projects distally out of the scatter body 71 (see detail view at the bottom right in FIG. 14). The cross-sectional area of the reinforcement element 95 is relatively small so that it throws few shadows distally. For this, it is also advantageous to design the stiffening element 95 as shortly as possible, whereas the stiffening effect of the needle tip end region 93 is larger than with a longer design of the spike 95.

Such a longer design of the spike 95 as a reinforcement element is shown in FIG. 15. Given a thinner design, the somewhat larger throwing of shadows can be neglected in comparison to the short spike 95 from FIG. 14. On account of the deeper embedding of the spike 95 into the scatter body 71, the spike 95 is better stabilised and can possibly project further distally out of the scatter body 71 (see detail views at the right in FIG. 15).

The basic percutaneous (through the skin 13) piercing of a light applicator 5 into tissue is illustrated in FIG. 16. The pierced skin 13 and the tissue 17 are widened by the distally tapering needle tip to such an extent that the light applicator 5 fits through. The sharper the needle tip, the gentler is this widening of the skin 13 and of the tissue 17 effected and the smaller is the force which the user must apply for this.

In FIG. 17, the reinforcement element 95 is configured as a triangular, thin sharp blade which is embedded into the cone-shaped scatter body 71 and projects distally as well as laterally out of the scatter body 71. The blade 95 defines a longitudinal section plane S1 which runs parallel to the longitudinal axis L of the light applicator 5. Given the piercing by the light applicator 5, the blade 95 pierces through and cuts the tissue to be passed, in order to simplify the widening of the tissue and to reduce the resistance. This makes particular sense given firm tissue 17 and for the penetration of tough skin layers.

An embodiment concerning which the scatter body 71 is pyramid shaped with an essentially square base surface is shown in FIG. 18. As is FIG. 19, the insertion section 11 of the light applicator 5 has a square cross section. The reinforcement element 95 here is likewise configured as a triangular, thin, sharp blade which however is embedded completely into the cone-shaped scatter body 71 and does not project or hardly projects distally or laterally out of the scatter body 71. The longitudinal section plane S1, in which the blade 95 lies, here is spanned by the diagonal of the square base surface of the scatter body 71 and the longitudinal axis L of the light applicator 5. The edges 97 of the scatter body 71 here form cutting edges which are reinforced by the blade 95 (see detailed views at the right in FIG. 19). In FIG. 19, the reinforcement element is shown as two blades which in cross section are arranged in a crossed manner at right angles to one another. By way of this, in particular a crossed cut arises on piercing, with which the tissue can be widened in a particularly simple manner.

As is shown in FIG. 20, the crossed blades 95 can be ground sharply at the cutting edge in different manners. The two blades 95 can each comprise corresponding slots 99, so that the blades can be inserted into one another in a crossed manner. The slots 99 each extend in the longitudinal direction over roughly half the blades 95. The width of the slots 99 corresponds roughly to the thickness of the blades 95.

Figure 21:
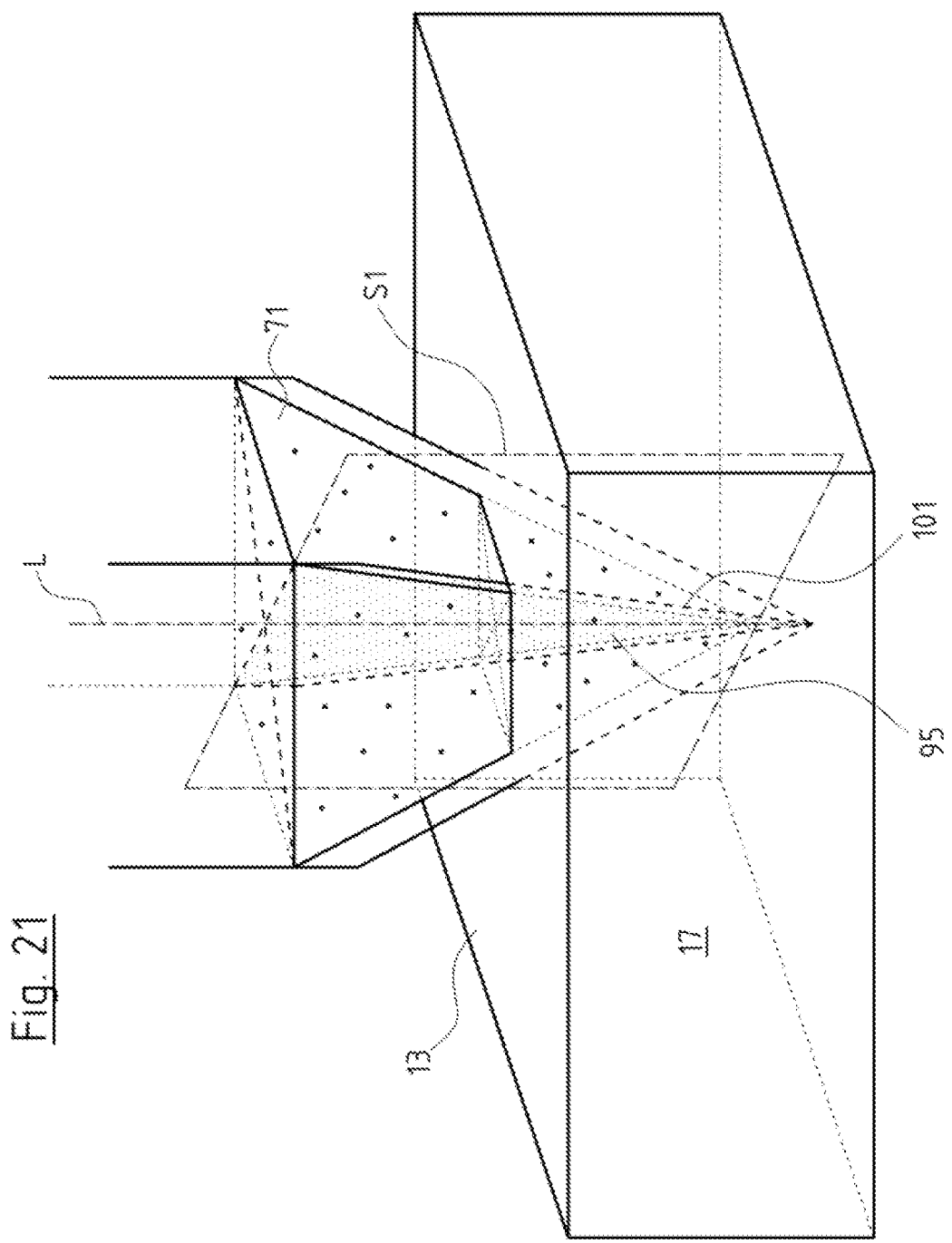
FIG. 21 is a schematic representation of the distal tip of a possible light applicator of an exemplary embodiment of the light applicator system disclosed herein, on piercing the skin of a patient.

It is clear from FIGS. 21 and 22 that even with a pyramid-shaped scatter body 71 with a square base surface, the reinforcement element 95 in the form of crossed blades 95 can project distally as well as laterally beyond the scatter body 71 for forming sharper cutting edges 101.

The reinforcement element 95 which is shown in FIG. 23 is a V-shaped blade, in order to reduce the light-impermeable area in the cutting plane which is formed by the blade 95 in the scatter body 71. Concerning the blades according to FIGS. 17 to 22, the blade however can be configured in a light-reflecting manner, so that this can be well compensated.

With regard to the embodiment examples which are shown in FIGS. 24 to 27, one deliberately makes do without a crossed configuration of two blades as a reinforcement element 95 and only one blade is used as a reinforcement element 95. The healing and scarring process of a crossed skin or tissue cut in some cases can run more poorly than a single longitudinal cut. Furthermore, the embedding of an individual blade 95 into the scatter body 71 is simpler with regard to manufacturing technology.

The scatter body 71 in the embodiment examples which are shown in the FIGS. 24 to 27 have a particular polyhedral shape with a square base surface. The scatter body 71 tapers distally in a pointed manner at a first angle α in a first longitudinal section plane S1 and in a second longitudinal section plane S2 which is perpendicular to the first longitudinal section plane S1 tapers distally in a pointed manner at as second angle ß, wherein the second angle ß is more acute than the first angle α. In the first longitudinal section plane S1, the blade 95 is embedded as a reinforcement element and projects distally, but not laterally, out of the scatter body 71. The cutting edges 101 of the blade 95 run at an angle α to one another and form a point 103. In the second longitudinal section plane S2, the tissue is not cut, but is gently pressed apart, and specifically not until the cut in the first longitudinal section plane S1 has already been made for the most part. The blunt angles of the edges of the scatter body 71 in the longitudinal section plane S2 contribute to the careful pressing part of the tissue on the longitudinal section plane S2.

The phases a-e of the skin or tissue opening when the needle tip has reached the respectively characterised penetration depth are shown in FIG. 24 at the bottom. Initially in phase a, one only cuts in the first longitudinal section plane S1 and in phase b the tissue is pressed apart only a little additionally in the second longitudinal section plane S2. In phase c, the cut in the first section plane S1 is completed. The large part of the widening of the skin and tissue opening in the second longitudinal section plane S2 does not take place until in the phases d and e, thus when the tissue opening has already been achieved by a defined cut.

The scatter body 71 according to the embodiment examples which are shown in the FIGS. 24 to 27 comprises a first proximal scatter body section 105 with a square cross section (see phase e). A second scatter body section 107 extends distally of the first scatter body section 105 and a third scatter body section 109 extends distally of the second scatter body section 107. The second scatter body section 107 has an essentially octagonal cross section (see phase d) and the third scatter body section 109 has an essentially rhombic cross section (see phases b and c). The reinforcement element 95 runs in the longitudinal section plane S1 along the longer rhombus diagonal in the third scatter body section 109.

As is shown in FIGS. 25 and 26, the blade 95 can also extend over the second scatter body section 107 and terminate laterally with the scatter body 71 (FIG. 25) or project laterally (FIG. 26). Given firmer tissue, a larger blade 95 (FIG. 26) can be advantageous and given softer tissue a smaller blade 95 (FIG. 25). The blade 95 which is shown in FIG. 26 and projects laterally beyond the cutter body 71 effects a defined tissue cut along the blade 95. Before the tissue tears open at an undefined other location by way of the process of the widening during the advance of the applicator, it should be cut open in the plane of the blade 95 in a targeted manner and herewith the tissue opening enlarged.

Figure 27:
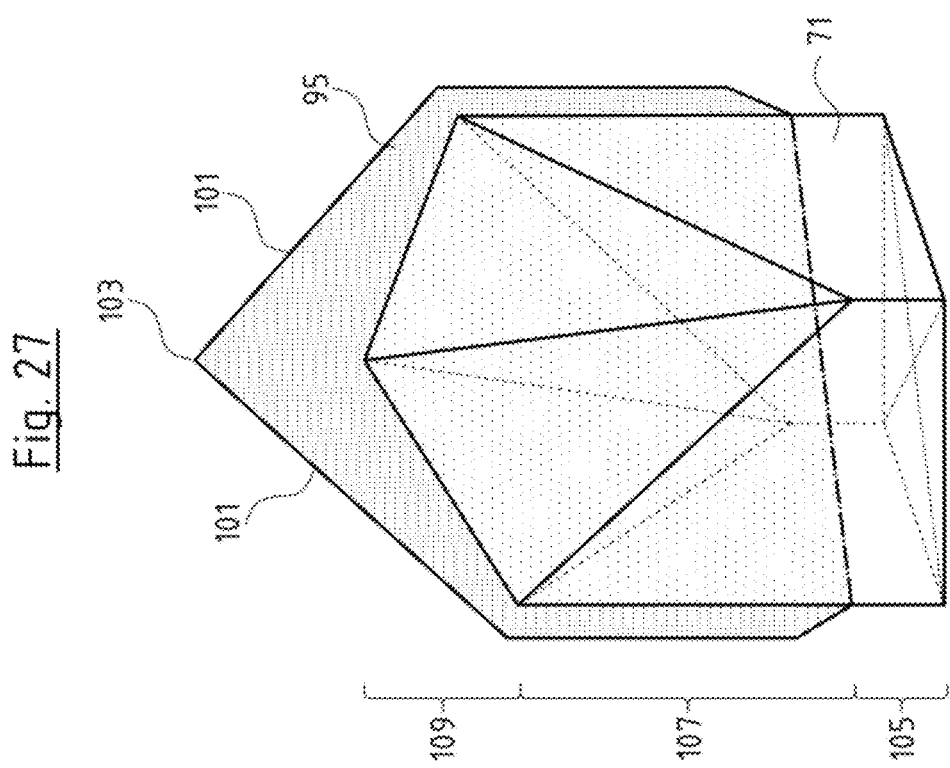
FIG. 27 is a schematic representation of the distal tip of a possible light applicator of another exemplary embodiment of the light applicator system disclosed herein.

An advantageous embodiment is shown in FIG. 27, concerning which the blade 95 as in FIG. 26 projects laterally and whose cutting edges 101 taper in a more pointed manner than the angle α and herewith forms a sharper point. The reinforcement element 95 therefore with the tip 103 projects further distally out of the scatter body 71 in the radial middle of the scatter body 71 than at the radial outer region of the scatter body 71. This simplifies the incision into form tissue, wherein amongst other things the force which is to be mustered by the user is reduced.

The numbered indications of the components or movement directions as "first", "second", "third" etc. have herein been selected purely randomly so as to differentiate the components or the movement directions amongst one another, and can also be selected in an arbitrarily different manner. Hence these entail no hierarchy of significance. A designation of a component or technical feature as "first" should not be misunderstood to the extent that there must be a second component or technical feature of this type. Moreover, any method steps, inasmuch as not explicitly stated otherwise or not compelling necessary, can be carried out in an arbitrary sequence and/or in a party or completely overlapping manner with regard to time.

Equivalent embodiments of the parameters, components or functions which are described herein and which appear to be evident to a person skilled in the art in light of this description are encompassed herein as if they were explicitly described. Accordingly, the scope of the protection is also to include equivalent embodiments. Features which are indicated as optional, advantageous, preferred, desired or similarly denoted "can"-features are to be understood as optional and as not limiting the protective scope.

The described embodiments are to be understood as illustrative examples and no not represent an exhaustive list of possible alternatives. Every feature which has been disclosed within the framework of an embodiment can be used alone or in combination with one or more other features independently of the embodiment, in which the features have been described. Whilst at least one embodiment is described and shown herein, modifications and alternative embodiments which appear to be evident to a person skilled in the art in the light of this description are included by the protective scope of this disclosure. Furthermore the term "comprise" herein is neither to exclude additional further features or method steps, nor does "one" exclude a plurality.

LIST OF REFERENCE NUMERALS 1 light applicator system
3 light applicator operation unit
5 light applicator
7 cable section of the light applicator
9 plug of the light applicator
11 insertion section of the light applicator
13 skin
15 healthy tissue
17 pathological tissue
19 LED
21 terminal of the light applicator operation unit
23 supply module
25 control module
27 organ
29 flat tape cable
31 working channel
33 shank
35 shank instrument
37 insertion section of the endoscope
39 picture sensor
41 first shank section
32 second shank section
45 third shank section
49, 49a, 49b encasing of the light applicator
50 first electrical contact of the LED
51 second electrical contact of the LED
53 adapter piece
55 metal half
57 metal half
59 insulator layer
61 electrical lead
61a first electrical lead
61b second electrical lead
63 contact receiver
65 contact receiver
67 sleeve
69 contact clip
71 scatter body
73 connection terminal
74 core of the first electrical lead
75 proximal needle tip section or the first thermal insulation layer
76 jacket of the first electrical led
77 second thermal insulation layer
79 third thermal insulation layer
80 deepening
81 end-face of the scatter body
82 widening
83 edge of the scatter body 84 undercut
85 tip of the scatter body
87 light-scattering material
89 light irradiated from the LED
91 light irradiated by the scatter body
93 needle tip end region of the scatter body
95 reinforcement element
97 edges of scatter body
99 slits in reinforcement element
101 cutting edges of the reinforcement element
103 tip of the reinforcement element
105 first scatter body section
107 second scatter body section
109 third scatter body section
A first light applicator section
B second light applicator section
C third light applicator section
D fourth light applicator section
S1 first longitudinal section plane
S2 second longitudinal section plane
α first angle
ß second angle

The invention claimed is:

1. A light applicator for examining and/or treating an organic body, the light applicator comprising:
a minimal-invasive, rigid, semi-flexible or flexible insertion section comprising a proximal end and a distal end, the insertion section extending along a longitudinal direction and the insertion section comprising an LED at the distal end thereof;
a first electrical lead for the supply of electricity to the LED, said lead extending in the insertion section in the longitudinal direction and the lead having a cross-sectional area of at least 70% of the cross-sectional area of the light applicator; and
radial thermal insulation, wherein the light applicator in the insertion section is thermally insulated in the radial direction by the radial thermal insulation where the radial thermal insulation reduces in a direction of the proximal end.

2. A light applicator according to claim 1, wherein the radial thermal insulation in the insertion section decreases stepwise and/or continuously in the direction of the proximal end.

3. A light applicator according to claim 1, wherein the radial thermal insulation in the insertion section comprises at least one radial thermal insulation layer, wherein a total thickness of the at least one thermal insulation layer reduces in the direction of the proximal end, the at least one radial thermal insulation layer comprising a thermal resistance, the thermal resistance of the at least one radial thermal insulation layer decreasing in the direction of the proximal end.

4. A light applicator according to claim 1, wherein the radial thermal insulation in the insertion section comprises a plurality of radial thermal insulation layers, wherein a number of thermal insulation layers decreases in the direction of the proximal end.

5. A light applicator according to claim 1, wherein a diameter of the first electrical lead increases to a same extent as the radial thermal insulation reduces in the direction of the proximal end.

6. A light applicator according to claim 1, wherein the cross-sectional area is essentially constant over a length of the insertion section.

7. A light applicator according to claim 1, wherein a thermal conductivity of a material of the radial thermal insulation in the insertion section reduces in the direction of the proximal end.

8. A light applicator according to claim 1, further comprising a second electrical lead for closing an electric circuit for the electricity supply of the LED, wherein the electrical second lead in the insertion section is configured more thinly than the first electrical lead where a cross-sectional area of the second electrical lead in the insertion section is less than 10% of the cross-sectional area of the light applicator.

9. A light applicator according to claim 8, wherein the second electrical lead in the insertion section is led along a side of the first electrical lead electrically insulated from the first electrical lead, in the form of a flat flexible circuit board or a thin enameled wire.

10. A light applicator according to claim 1, wherein the first electrical lead at least in sections in the insertion section is configured as a flexible strand bundle.

11. A light applicator according to claim 1, wherein the first electrical lead comprises at least one deepening and/or widening at a position outside of the insertion section.

12. A light applicator according to claim 1, further comprising a cable section wherein the insertion section is configured as a rigid needle section, wherein the first electrical lead stiffens the insertion section and wherein the cable section is fixedly connected or releasably connectable to the needle section at a proximal side.

13. A light applicator according to claim 12, wherein the first electrical lead comprises a core with a first material and a jacket with a second material, wherein the first material is more thermally conductive than the second material and the second material is more flexurally rigid than the first material.

14. A light applicator according to claim 13, wherein the first material comprises copper, aluminum or silver and the second material comprises steel.

15. A light applicator according to claim 13, wherein a cross-sectional area of the core is more than 40% of a cross-sectional area of the first electrical lead.

16. A light applicator according to claim 13, wherein a cross-sectional area of the core is 0.8 to 1.2 times a cross-sectional area of the LED.

17. A light applicator according to claim 1, wherein a cross-sectional area of the first electrical lead is at least as large as a cross-sectional area of the LED.

18. A light applicator according to claim 1, wherein the LED is in electrical and thermally-conductive contact with a distal end-face of the first electrical lead.

19. A light applicator according to claim 1, wherein the insertion section comprises a needle tip which is arranged at least partly distally of the LED and tapers distally, and comprises a light-transparent scatter body for scattering the light of the LED.

20. A light applicator according to claim 19, wherein a volume of the needle tip is essentially formed by the scatter body and in a pointed and/or edge needle tip end region comprises a reinforcement element.

21. A light applicator according to claim 20, wherein the scatter body is configured essentially of a light-scattering plastic or light-transparent plastic with light-scattering particles and the reinforcement element is formed from metal.

22. A light applicator according to claim 20, wherein the reinforcement element is configured as a spike which is embedded at least partly into the scatter body or as a blade which is embedded at least partly into the scatter body.

23. A light applicator according to claim 20, wherein the reinforcement element projects at least partly distally and/or laterally out of the scatter body.

24. A light applicator according to claim 23, wherein the reinforcement element in a radial center of the scatter body projects out of the scatter body further distally than at a radial outer region of the scatter body.

25. A light applicator according to claim 20, wherein the reinforcement element at a lateral side has a mirroring surface.

26. A light applicator according to claim 19, wherein the scatter body in a first longitudinal section plane tapers distally to a point configuration at a first angle and in a second longitudinal section plane which lies perpendicularly to the first longitudinal section plane tapers distally to a point at a second angle, wherein the second angle is more acute than the first angle.

27. A light applicator according to claim 26, wherein the reinforcement element is arranged in the first longitudinal section plane and reinforces an edge needle tip end region which runs therein.

28. A light applicator according to claim 19, wherein the scatter body is polyhedral with a first scatter body section, a second scatter body section which is arranged distally of the first scatter body section and a third scatter body section which is arranged distally of the second scatter body section, wherein the first scatter body section has an essentially square cross section, wherein the second scatter body section has an essentially octagonal cross section and wherein the third scatter body section has an essentially rhomboidal cross section.

29. A light applicator according to claim 28, wherein the reinforcement element runs along a longest rhomboid diagonal in the third scatter body section.

30. A light applicator according to claim 20, wherein the reinforcement element projects at least partly laterally out of the scatter body.

31. A light application according to claim 20, wherein the reinforcement element is configured as two blades which in cross section are arranged crossed with respect to one another.

* * * * *